United States Patent
Bai et al.

(10) Patent No.: US 10,190,053 B2
(45) Date of Patent: Jan. 29, 2019

(54) PYROLYSIS OF LIGNIN

(71) Applicant: Iowa State University Research Foundation, Inc., Ames, IA (US)

(72) Inventors: Xianglan Bai, Ames, IA (US); Shuai Zhou, Atlanta, GA (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

(21) Appl. No.: 15/432,798

(22) Filed: Feb. 14, 2017

(65) Prior Publication Data

US 2017/0240934 A1  Aug. 24, 2017

Related U.S. Application Data

(60) Provisional application No. 62/297,605, filed on Feb. 19, 2016.

(51) Int. Cl.
| | |
|---|---|
| C10B 49/10 | (2006.01) |
| C10B 53/02 | (2006.01) |
| C10B 57/08 | (2006.01) |
| C10B 57/06 | (2006.01) |

(52) U.S. Cl.
CPC .............. *C10B 49/10* (2013.01); *C10B 53/02* (2013.01); *C10B 57/06* (2013.01); *C10B 57/08* (2013.01); *C12P 2201/00* (2013.01); *Y02E 50/14* (2013.01)

(58) Field of Classification Search
CPC ......... C12P 7/649; C10B 49/10; C10B 53/02; C10B 57/12
See application file for complete search history.

(56) References Cited

U.S. PATENT DOCUMENTS

| | | | | |
|---|---|---|---|---|
| 5,807,952 A | * | 9/1998 | Agblevor | C07B 41/02 527/400 |
| 2012/0047794 A1 | * | 3/2012 | Bartek | C10B 49/16 44/307 |

FOREIGN PATENT DOCUMENTS

WO    2011159154 A1    12/2011

OTHER PUBLICATIONS

Goldstein, I.S. (1981) Organic Chemicals from Biomass, CRC Press, 320 pgs (Office action cites p. 74).*
Bridgewater, A.V. et al. (2000) Renewable and Sustainable Energy Reviews, 4, 1-73.*
Silverstein et al., "A Comparison of Chemical Pretreatment Methods for Improving Saccharification of Cotton Stalks," Bioresource Technology 98:3000-3011 (2007).
Beis et al., "Fast Pyrolysis of Lignins," BioResources 5(3):1408-1424 (2010).

(Continued)

*Primary Examiner* — Brian A McCaig
(74) *Attorney, Agent, or Firm* — LeClairRyan PLLC

(57) ABSTRACT

One aspect of the present invention relates to a method of modifying thermoplastic properties of lignin rich biomass to reduce agglomeration during any subsequent pyrolysis. The method comprises providing a lignin rich biomass and treating the lignin rich biomass with an alkali metal hydroxide or an alkaline earth metal hydroxide under conditions effective to reduce agglomeration, during any subsequent pyrolysis, compared to when the lignin rich biomass is not subjected to said treating. Also disclosed is a method of fast pyrolysis using the product of this method of modifying the thermoplastic properties of lignin rich biomass.

13 Claims, 15 Drawing Sheets

(56) References Cited

OTHER PUBLICATIONS deWild et al., "Pyrolysis of Wheat Straw-Derived Organosolv Lignin," Journal of Analytical and Applied Pyrolysis 93:95-103 (2012).

Misson et al., "Pretreatment of Empty Palm Fruit Bunch for Production of Chemicals via Catalytic Pyrolysis," Bioresource Technology 100:2867-2873 (2009).

Mukkamala et al., "Formate-Assisted Fast Pyrolysis of Lignin," Energy Fuels 26:1380-1384 (2012).

Nowakowski et al., "Lignin Fast Pyrolysis: Results from an International Collaboration," Journal of Analytical and Applied Pyrolysis 88:53-72 (2010).

DeWild et al., "Thermolysis of Lignin for Value-Added Products," Meeting of the International Humic Substances Society, Tenerife, Canary Islands, 27 pp., Jun. 27-Jul. 2, 2010.

Gyftopoulou, E, "Fast Pyrolysis of Lignin," Bio-Energy Research Group, PyNe Meeting, Vicenza, 27 pp., Oct. 12, 2007.

Palmisano et al., "Fluidized Bed Pyrolysis of Lignin in a Bubbling Bed Reactor," Bio-Energy Conference III, Canary Islands, Spain, 20 pp., May 22-27, 2011.

Ragauskas et al., "Lignin Valorization: Improving Lignin Processing in the Biorefinery," Science 344, 1246843 (2014).

Trinh et al., "Fast Pyrolysis of Lignin Using a Pyrolysis Centrifuge Reactor," Energy Fuels 27:3802-3810 (2013).

Venderbosch et al., "Fast Pyrolysis Technology Development," Biofuels, Bioprod. Bioref. 4:178-208 (2010).

Wyman et al., "Coordinated Development of Leading Biomass Pretreatment Technologies," Bioresource Technology 96:1959-1966 (2005).

Zhou et al., "The Use of Calcium Hydroxide Pretreatment to Overcome Agglomeration of Technical Lignin During Fast Pyrolysis," Green Chem. 17:4748-4759 (2015).

Thomas et al., "A Supercritical Water Approach to Cellulosic Sugars: Lifecycle Energy, Greenhouse Gas and Water Implications," Renmatix LCA, 11 pp. (2012).

Vishtal et al., "Challenges in Industrial Applications of Technical Lignins," BioResources 6(3):3547-3568 (2011).

* cited by examiner

PYROLYSIS OF LIGNIN

This application claims the benefit of U.S. Provisional Patent Application Ser. No. 62/297,605, filed Feb. 19, 2016, which is hereby incorporated by reference in its entirety.

FIELD OF THE INVENTION

The present invention relates to the preparation of lignin for fast pyrolysis.

BACKGROUND OF THE INVENTION

Lignin is the second most abundant natural polymer in the biosphere followed by cellulose, accounting for up to 30% of lignocellulosic biomass. Over 50 million tons of so-called technical lignin is annually extracted from lignocellulosic biomass as a byproduct of the pulp and paper industry with increasing amounts from the emerging cellulosic ethanol industry (Ragauskas et al., "Lignin Valorization: Improving Lignin Processing in the Biorefinery," *Science* 344(6185): 1246843 (2014) and Azadi et al., "Liquid Fuels, Hydrogen and Chemicals from Lignin: a Critical Review," *Renew. Sust. Energ. Rev.* 21:506-523 (2013)). Lignin is a phenylpropane-based polymer biosynthesized from random polymerization of three precursor monomers. Because of its abundance and availability in low cost, lignin has potential as a renewable source of aromatics. At present, most lignin is burned as boiler fuel while only 2% of it is upgraded to biobased products, such as binder, resin, and dispersant (Huber et al., "Synthesis of Transportation Fuels from Biomass: Chemistry, Catalysts, and Engineering," *Chem. Rev.* 106:4044-4098 (2006); Zakzeski et al., "The Catalytic Valorization of Lignin for the Production of Renewable Chemicals," *Chem. Rev.* 110:3552-99 (2010); Effendi et al., "Production of Renewable Phenolic Resins by Thermochemical Conversion of Biomass: A Review," *Renew. Sust. Energ. Rev.* 12:2092-2116 (2008); and Lange et al., "Oxidative Upgrade of Lignin—Recent Routes Reviewed," *Eur. Polym. J.* 49:1151-1173 (2013)). Developing effective upgrading methods to convert lignin into value-added products could reduce dependency on petroleum and also improve the economic prospects for companies producing lignin as a co-product of biomass processing.

Depolymerizing lignin by either biological or thermochemical means has been extensively studied over the past several decades (Perez et al., "Biodegradation and Biological Treatments of Cellulose, Hemicellulose and Lignin: An Overview," *Int. Microbiol.* 5:53-63 (2002); Salvachua et al., "Towards Lignin Consolidated Bioprocessing: Simultaneous Lignin Depolymerization and Product Generation by Bacteria," *Green Chem.* 17:4951-4967 (2015); Pandey et al., "Lignin Depolymerization and Conversion: a Review of Thermochemical Methods," *Chem. Eng. Technol.* 34:29-41 (2011); and Amen-Chen et al., "Production of Monomeric Phenols by Thermochemical Conversion of Biomass: A Review," *Bioresource Technol.* 79:277-299 (2001)). Solvent liquefaction using a variety of solvents at elevated temperatures and pressures is the most common method for deconstructing lignin (Jin et al., "Liquefaction of Lignin by Polyethyleneglycol and Glycerol," *Bioresource Technol.* 102:3581-3583 (2011); Kang et al., "Hydrothermal Conversion of Lignin: A Review," *Renew. Sust. Energ. Rev.* 27:546-558 (2013) and Kleinert et al., "Optimizing Solvolysis Conditions for Integrated Depolymerisation and Hydrodeoxygenation of Lignin to Produce Liquid Biofuel," *J. Anal., Appl. Pyrol.* 85:108-117 (2009)). Despite the advantages of solvent liquefaction, the consumption of solvent and the need for separating reaction products from solvent, char and/or catalysts present both economic and technical challenges.

Fast pyrolysis is an alternative thermal depolymerization technique. Fast pyrolysis has been widely explored for the conversion of whole plant biomass into liquid products (Bridgwater et al., "An Overview of Fast Pyrolysis of Biomass," *Org. Geochem.* 30:1479-1493 (1999); Mohan et al., "Pyrolysis of Wood/Biomass for Bio-Oil: A Critical Review," *Energ. Fuel* 20:848-889 (2006) and Bridgwater "Upgrading Biomass Fast Pyrolysis Liquids," *Environ. Prog. Sust. Energ.* 31:261-268 (2012)). Fast pyrolysis rapidly heats the feedstock (usually <2 s) in the absence of oxygen and usually at atmospheric pressure. Lignocellulosic biomass is substantially decomposed to form liquid, called bio-oil, char, and non-condensable gases. Bio-oil from fast pyrolysis is similar to the liquid produced by solvent liquefaction. It can be upgraded to hydrocarbon fuels or other chemicals. The char product (also known as biochar) has several applications such as solid fuel, soil amendment and activated carbon (Laird et al., "Review of the Pyrolysis Platform for Coproducing Bio-Oil and Biochar," *Biofuel Bioprod Bior.* 3:547-562 (2009)).

Despite its potential, fast pyrolysis of technical lignin has been infrequently studied, usually limited to batch experiments involving only small quantities of lignin (Ben et al., "Pyrolysis of Kraft Ligning with Additives," *Energ. Fuel* 25:4662-4668 (2011); Kosa et al., "Pyrolysis Oils from $CO_2$ Precipitated Kraft Lignin," *Green Chem.* 13:3196-3202 (2011) and Sharma et al., "Characterization of Chars From Pyrolysis of Lignin," *Fuel* 83:1469-1482 (2004)). Although these previous studies have provided valuable insight into lignin depolymerization, continuous pyrolysis relevant to commercial applications are lacking (De Wild et al., "Lignin Pyrolysis for Profitable Lignocellulosic Biorefineries," *Biofuel Bioprod. Bior.* 8:645-657 (2014)). Efforts to continuously pyrolyze lignin have been largely unsuccessful due to the melting and subsequent agglomeration of lignin particles to form "hard shell" solid material, which clogs the reactor and forces shut-down. This problem was highlighted by an international collaboration in 2010 (Nowakowski et al., "Lignin Fast Pyrolysis: Results From an International Collaboration," *J. Anal., Appl. Pyrol.* 88:53-72 (2010)). Two types of lignin, one from soda pulping of non-woody biomass and the other from weak acid hydrolysis of softwood, were distributed to seven laboratories for pyrolysis in smallscale, fluidized bed pyrolyzer. None of the laboratories were able to pyrolyze the soda pulp lignin due to plugging of the feeder or defluidization of the reactor. Pyrolysis of the acid hydrolysis lignin was only marginally better, possibly because of the presence of a large amount of carbohydrate in this particular feedstock.

Several researchers have attempted to pyrolyze lignin by adding cooling jackets or making other design changes to the feeder tubes, installing mechanical stirrers inside the reactors, pelletizing lignin, or performing pyrolysis in the presence of oxygen (Li et al., "Oxidative Pyrolysis of Kraft Lignin in a Bubbling Fluidized Bed Reactor With Air," *Biomass Bioenerg.* 76:96-107 (2015); Trinh et al., "Fast Pyrolysis of Lignin Using a Pyrolysis Centrifuge Reactor," *Energ. Fuel* 27:3802-3810 (2013); and Tumbalam Gooty et al., "Kraft-Lignin Pyrolysis and Fractional Condensation of its Bio-Oil Vapors," *J. Anal., Pyrol.* 106:33-40 (2014)). None of these efforts were completely successful in eliminating agglomeration. In a recent review paper, Ragauskas et al., "Lignin Valorization: Improving Lignin Processing in the Biorefinery," *Science* 344(6185):1246843 (2014) warned that the inability to continuously feed lignin to large-scale reactors is the primary technical barrier to pyrolyzing lignin for the production of fuels and chemicals.

Pretreating lignin is another approach to improving the pyrolysis of lignin. Mukkamala et al., "Formate-assisted Fast Pyrolysis of Lignin," *Energ. Fuel* 26:1380-1384 (2012) pretreated an acid hydrolyzed kraft lignin with 50-100% weight equivalence of calcium formate using a two-step process before pyrolysis in an entrained flow reactor. In their study, fluidizing sand was removed from the reactor during pyrolysis in order to avoid agglomeration between sand and lignin particles. WO 2011159154 A1 to Wilberink et al. describes a slurry of lignin and clay (1:1 weight ratio) mixed in water and extruded as pellets and then dried in a two-step heat treatment prior to pyrolysis. Upon pyrolysis in an auger reactor, phenolic-rich bio-oil was produced. The solid residue from pyrolysis of lignin-clay pellets were pellets containing char and the clay binder. See Wilberink et al. De Wild et al., "Lignin Pyrolysis for Profitable Lignocellulosic Biorefineries," *Biofuel Bioprod. Bior.* 8:645-657 (2014) also pyrolyzed in a fluidized bed the pellets formed from the lignin co-product of organosolv processing of straw. They concluded that a dedicated feeding system and careful control of pyrolysis conditions are required to pyrolyze lignin even when pelletized.

Because of this difficulty of pyrolyzing lignin, the products of lignin pyrolysis have yet to be fully characterized. One previous study reported the composition of pyrolysis vapor but not char (De Wild et al., "Lignin Pyrolysis for Profitable Lignocellulosic Biorefineries," *Biofuel Bioprod. Bior.* 8:645-657 (2014)). A study conducted by Sharma et al., "Characterization of Chars From Pyrolysis of Lignin," *Fuel* 83:1469-1482 (2004) characterized the agglomerated char produced from slow pyrolysis of lignin in a batch reactor but did not give information about volatile products.

The present invention is directed to overcoming the deficiencies in the art by treating lignin to prevent its melting and subsequence agglomeration upon heating, and preventing difficulties that can arise from lignin agglomeration during pyrolysis, and allowing for continuous pyrolysis in a fluidized reactor.

SUMMARY OF THE INVENTION

One aspect of the present invention relates to a method of modifying thermoplastic properties of lignin rich biomass to reduce agglomeration during any subsequent pyrolysis. The method comprises providing a lignin rich biomass and treating the lignin rich biomass with an alkali metal hydroxide or an alkaline earth metal hydroxide under conditions effective to reduce agglomeration, during any subsequent pyrolysis, compared to when the lignin rich biomass is not subjected to said treating.

Another aspect of the present invention relates to a method of fast pyrolysis. The method comprises providing a lignin rich biomass, treating the lignin rich biomass with an alkali metal hydroxide or an alkaline earth metal hydroxide under conditions effective to reduce agglomeration, during pyrolysis, compared to when the lignin rich biomass is not subjected to said treating, and pyrolyzing the treated lignin rich biomass to produce pyrolysis products.

Applicants believe that lignin would have to be chemically modified to prevent its melting and subsequent agglomeration upon heating. The present invention is a simple chemical pretreatment of lignin that prevents its agglomeration. The properties of the resulting pyrolysis products are described, and applicants propose a mechanism by which pretreatment prevents lignin agglomeration.

The benefits of the present invention include the ability to fast pyrolyze lignin without modifying existing equipment. The alkali metal hydroxide or alkaline earth metal hydroxides are present in low ratios to lignin rich biomass, have low material cost, high availability, are easy to recover by burning char and leaching the ash with water, and some have low risk hazard. The heat of combustion from this regeneration process can be used to heat the pyrolyzer. Reduced agglomeration of lignin during fast pyrolysis creates the opportunity for producing liquid products rich in phenolic monomers and dimers, which could be used as chemicals or upgraded for hydrocarbon fuels, and bio-char, which could be used as fertilizer. This would be achieved with reduced handling time and operating costs compared to solvent liquefaction methods for processing lignin. In addition, the pretreatment process could be integrated into the lignin extraction process, further reducing operating costs.

BRIEF DESCRIPTION OF THE DRAWINGS

FIG. 1A shows untreated lignin. FIG. 1B shows pretreated lignin. FIG. 1C shows char/sand agglomerates recovered from the pyrolysis of untreated lignin. FIG. 1D shows char recovered from pyrolysis of pretreated lignin.

FIG. 2A shows pyrolysis char from untreated supercritical hydrolysis lignin. FIG. 2B shows pyrolysis char from pretreated supercritical hydrolysis lignin. FIG. 2C shows pyrolysis char from untreated enzymatic hydrolysis lignin. FIG. 2D shows pyrolysis char from pretreated enzymatic hydrolysis lignin. FIG. 2E shows pyrolysis char from untreated alkali lignin. FIG. 2F shows pyrolysis char from pretreated alkali lignin. The chars shown in FIG. 2A and FIG. 2B are recovered from the fluidized reactor, and the chars shown in FIGS. 2C-F are recovered from sample cups in a TGA oven. The circular shaped agglomerated char in FIG. 2C is due to the cylindrical sample cup.

FIG. 5A shows the GC/MS chromatogram of heavy oil, and FIG. 5B shows the GC/MS chromatogram of light oil.

FIG. 7A shows an SEM image of char obtained from the pyrolysis of untreated lignin. FIG. 7B shows an SEM image of char obtained from the pyrolysis of pretreated lignin.

FIG. 11A shows the spectrum at the frequency range of 1750-4000 cm$^{-1}$. The characteristic IR absorption frequency of reduced OH groups is marked at 1. FIG. 11B shows the spectrum at the frequency range of 650-1750 cm$^{-1}$. The characteristic IR absorption frequency of reduced aldehyde groups is marked at 2, and characteristic IR absorption frequency of the formation of alcohol groups is marked at 3.

DETAILED DESCRIPTION OF THE INVENTION

Figure 1:
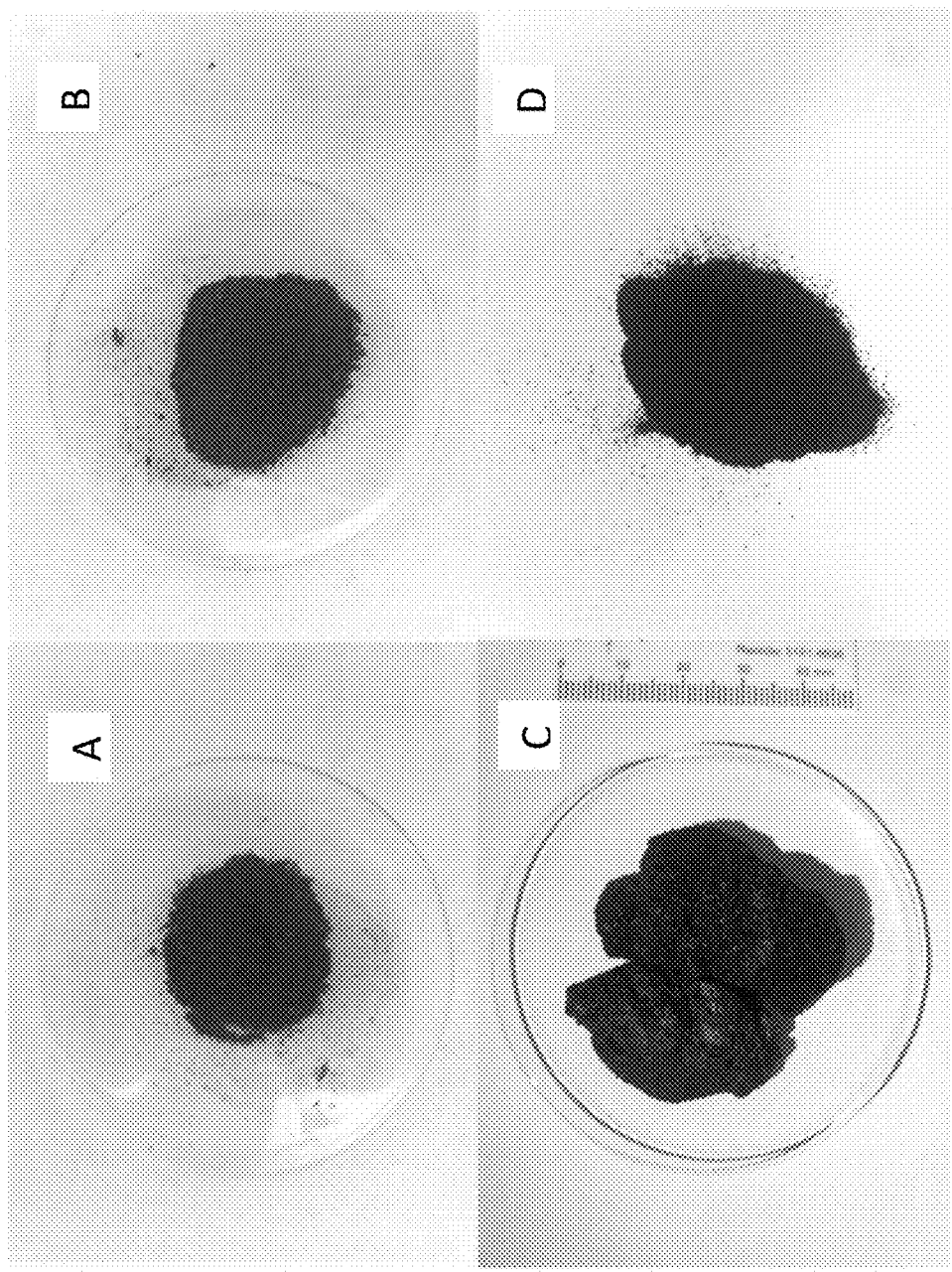
FIGS. 1A-D show organosolv lignin feedstocks and solid products recovered from the fluidized bed after pyrolysis.
Figure 2:
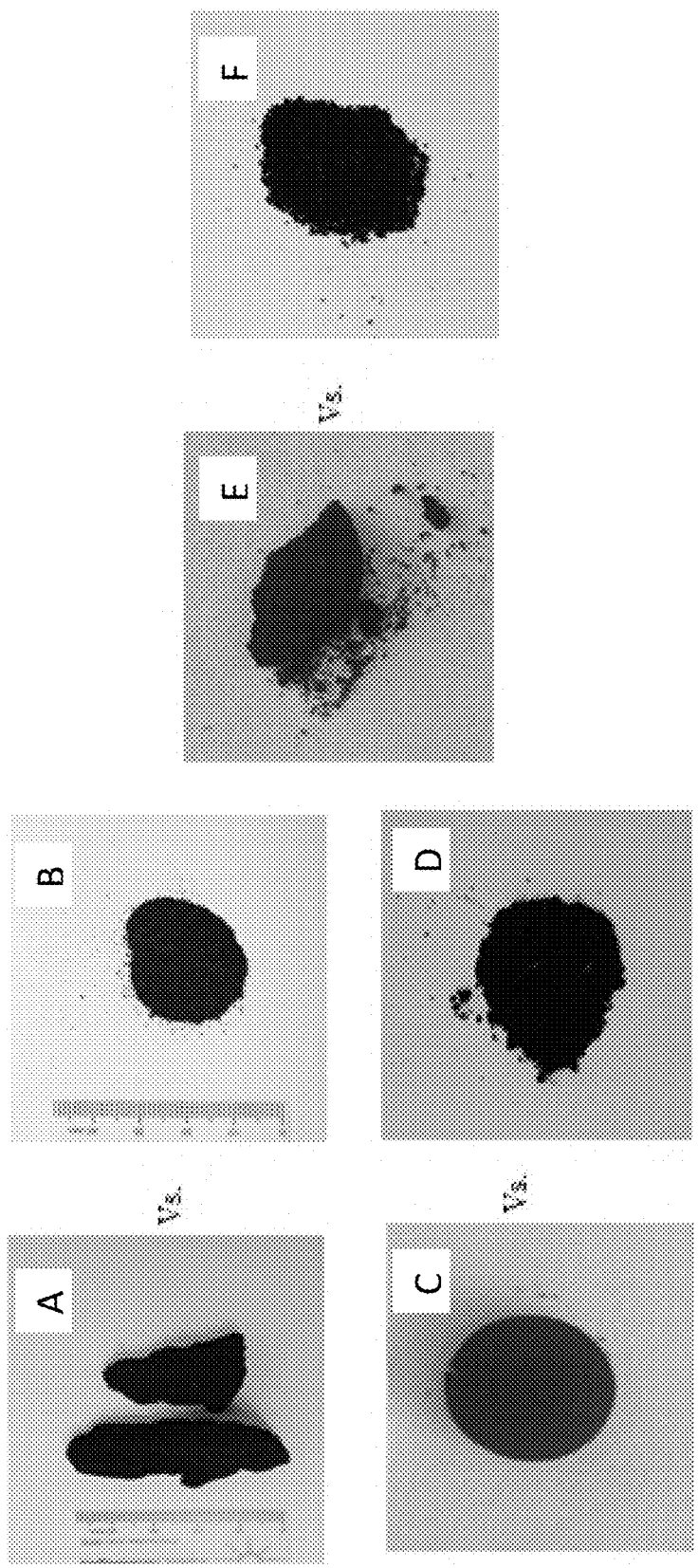
FIGS. 2A-F show comparisons of pyrolysis chars produced from untreated and pretreated lignins.

One aspect of the present invention relates to a method of modifying thermoplastic properties of lignin rich biomass to reduce agglomeration during any subsequent pyrolysis. The method comprises providing a lignin rich biomass, and treating the lignin rich biomass with an alkali metal hydroxide or an alkaline earth metal hydroxide under conditions effective to reduce agglomeration, during any subsequent pyrolysis, compared to when the lignin rich biomass is not subjected to said treating.

As used herein, the terms "biomass," "lignin rich biomass," or "lignocellulosic biomass" refer to any plant material, vegetation, or vegetative agricultural waste from any source that can be used to supply lignin to be used in any of the methods of the present invention where a source of lignin is used. Lignin rich biomass may include any naturally occurring terrestrial plants and energy crops as well as processed materials such as forestry residues, mill residues, and agricultural residues, and any lignin derivatives. Exemplary lignin rich biomass includes, without limitation, corn stover, sugarcane bagasse, wheat straw, saw mill and paper mill discards (e.g., pine saw dust). Energy crops are crops with a high yield of lignocellulosic biomass (e.g., switch grass).

"Lignin" is a polyphenolic material comprised of methoxylated phenyl propane units linked by ether and carbon-carbon bonds. Lignins can be highly branched and can also be crosslinked. Lignins can have significant structural variation that depends, at least in part, on the plant source involved. Lignin fills spaces in the cell wall and between cellulose, hemicellulose, and, if present, pectin components.

As used herein, the term "native lignin" refers to lignin in its natural state, in plant material.

Native lignin is a naturally occurring amorphous complex cross-linked organic macromolecule that comprises an integral component of all plant biomass. The chemical structure of lignin is irregular in the sense that different structural units (e.g., phenylpropane units) are not linked to each other in any systematic order. Extracting native lignin from lignocellulosic biomass generally results in lignin fragmentation into numerous mixtures of irregular components. Furthermore, the lignin fragments may react with any chemicals employed in the extraction process. Consequently, the generated lignin fractions can be referred to as lignin derivatives and/or technical lignins.

As it is difficult to elucidate and characterize such complex mixture of molecules, lignin derivatives are usually described in terms of the lignocellulosic plant material used, and the methods by which they are generated and recovered from lignocellulosic plant material, i.e., hardwood lignins, softwood lignins, and annual fiber lignins. Each type of extraction process used to separate lignocellulosic components produces lignin derivatives that are very different in their physico-chemical, biochemical, and structural properties.

As used herein, the terms "lignin derivatives" and "derivatives of native lignin" refer to lignin material extracted from lignocellulosic biomass, using any mechanical or chemical means. Usually, such material will be a mixture of chemical compounds that are generated during the extraction process. A lignin derivative may include a lignin mimic.

A "lignin mimic" can refer to a compound, either chemically synthesized or in its natural form, that is capable of mimicking the conformation and desirable features of a natural lignin.

Non-limiting examples of lignin derivatives include kraft lignin, soda lignin, lignosulphonates, organosolv lignin, hydrolysis lignin, ionic liquid lignin (Vishtal et al., "Challenges in Industrial Applications of Technical Lignins" BioResources 6(3):3547-3568 (2011), which is hereby incorporated by reference in its entirety), and supercritical hydrolysis lignin. These lignin derivatives are typically isolated as by-product streams in lignocellulosic refineries, have a modified structure, and contain impurities that are dependent on the processing method. Id.

Kraft lignin is produced in the sulphate (kraft) cooking process (Vishtal et al., "Challenges in Industrial Applications of Technical Lignins" BioResources 6(3):3547-3568 (2011), which is hereby incorporated by reference in its entirety). Most of the lignin in the biomass is dissolved in a solution of sodium hydroxide and sodium sulfide, and degraded into fragments of varying molecular weight, which are soluble in alkali solutions. Id. The solutions are later neutralized. Id. It contains an increased amount of phenolic hydroxyl groups, and may be further characterized by the formation of some biphenyl and other condensed structures, formation of quinine and catechol structures, increased amount of carboxyl groups, and high ash content. Id. This process may also be referred to as alkaline extraction process.

Soda lignin is produced during the soda or soda-anthraquinone pulping process, mainly from annual crops such as flax, straws, and bagasse, as well as some hardwoods. Vishtal et al., "Challenges in Industrial Applications of Technical Lignins" BioResources 6(3):3547-3568 (2011), which is hereby incorporated by reference in its entirety. Unlike the kraft process, the cooking liquor and resulting lignin derivative is sulphur-free. Id. Soda lignin from non-wood plants may be characterized by increased p-hydroxyl units and carboxyl groups, as well as high silica and nitrogen contents. Id.

Lignosulphonates are produced during sulphite cooking, in which wood is delignified by means of $HSO_3^-$ and $SO_3^{2-}$ ions. Vishtal et al., "Challenges in Industrial Applications of Technical Lignins" BioResources 6(3):3547-3568 (2011), which is hereby incorporated by reference in its entirety. Lignin is sulphonated, degraded, and solubilized during the process. Id. Lignosulphonates may be characterized by a variety of functional groups including phenolic hydroxyl groups, carboxylic groups, and sulphur containing groups. Id. These and other structural features provide unique colloidal properties. Id.

Organosolv lignin is produced through a pulping process in which an organic solvent or mixture of organic solvents and water is used as a cooking medium. Vishtal et al., "Challenges in Industrial Applications of Technical Lignins" *BioResources* 6(3):3547-3568 (2011), which is hereby incorporated by reference in its entirety. Solvents may include acetic acid, formic acid, ethanol, or peroxiorganic acids. Id. Organosolv lignin is separated via solubilization, leading to a less modified lignin with a higher homogeneity than lignosulphonates or alkali lignins. Id. It may be characterized as having low molecular weight and high chemical purity, poor solubility, and many reactive side chains available for further chemical reactions. Id. FormicoFib, Alcell, Acetosolv, Organocell, and ASAM are examples of commercialized registered organosolv processes. Id.

Hydrolysis lignin is produced during dilute acid hydrolysis of wood. Vishtal et al., "Challenges in Industrial Applications of Technical Lignins" *BioResources* 6(3): 3547-3568 (2011), which is hereby incorporated by reference in its entirety. It may be characterized by higher activity than lignosulphonates and kraft lignin, increased amount of condensed structures with high molecular weight, and high sorption. Id. Hydrolysis lignin may be further classified by the type of hydrolysis process (i.e. enzymatic hydrolysis lignin or acid hydrolysis lignin), and by the origin (i.e. softwood, hardwood, and non-wood). Id. Acid hydrolysis may utilize either organic (i.e. formic, acetic) or inorganic (i.e. sulphuric, hydrochloric) acids. Id.

Supercritical hydrolysis uses supercritical water to break down cellulose into usable sugars. Thomas et al., "A Supercritical Water Approach to Cellulosic Sugars: Lifecycle Energy, Greenhouse Gas and Water Implications" *Renmatix LCA* (2012), which is hereby incorporated by reference in its entirety. Lignin is found in the solid fraction, and further extracted using cellulose hydrolysis in the following manner: the solid fraction is mixed with water, heated, and then treated with supercritical water. Id. The output is a cellulose liquor and lignin. Id.

Ionic liquid lignins are comprised of organic salts that remain as liquids at relatively low temperatures, and several such ionic liquids have been found to be able to fractionate lignocellulosic materials. Vishtal et al., "Challenges in Industrial Applications of Technical Lignins" *BioResources* 6(3):3547-3568 (2011), which is hereby incorporated by reference in its entirety. The properties of ionic liquid lignin are similar to organosolv lignin. Id. Lignin can be recovered from the ionic liquid through precipitation, and the ionic liquid can be recycled. Id.

In one embodiment of the present invention, the lignin rich biomass has a lignin content of at least 50%. In other embodiments, the lignin rich biomass has a lignin content of at least 60%, at least 70%, or at least 80%.

In another embodiment of the present invention, the lignin rich biomass is a lignin derivative. In this embodiment, it is contemplated that the lignin derivative may be produced by a process selected from the group consisting of organosolv process, supercritical hydrolysis, enzymatic hydrolysis, acid hydrolysis, alkaline extraction solvent extraction, ionic-liquid extraction, and aprotic solvent extraction.

As used herein, the term "thermoplastic properties" refers to the temperature dependent pliability or mold-ability of a material. Thermoplastic properties may be retained during subsequent heating and cooling cycles (i.e. thermoplastic), or be lost after initial heating and cooling (i.e. thermoset). Lignin is an amorphous polymer, and behaves as a thermoplastic material, undergoing a glass transition at temperatures which vary widely depending on the method of isolated, water content, and heat treatment.

The thermoplastic properties of lignin, including low melting temperature, can lead to melting and subsequent agglomeration under conditions such as pyrolysis. As used herein, "agglomeration" refers to the formation of more or less firmly bound primary particles by collision processes between melted particles, primary particles and agglomerates, as well as pre-existing agglomerates. Agglomeration may be between similar or dissimilar particles. For example, agglomeration may be between lignin particles, between lignin and sand particles, or lignin and char particles. Agglomeration during pyrolysis may lead to difficulty in product recovery or cleaning of any the reactor. Furthermore, the melting and agglomeration that occurs during pyrolysis of technical lignins can lead to clogging of the reactor and defluidization of the sand bed, forcing shutdown and preventing continuous pyrolysis.

Pyrolysis is the thermochemical decomposition of biomass at elevated temperatures in the absence of oxygen. The temperatures of pyrolysis are typically around 300 to 550° C. When treated at these temperatures, biomass decomposes to three primary products, namely, char, bio-oil, and gases (e.g., CO, $H_2$, $CO_2$, and $CH_4$). Fast pyrolysis, i.e., the rapid thermal decomposition of organic compounds in the absence of oxygen to produce liquids, gases, and chars, results in glycosidic bond breaking, liberating anhydrosugars in a process referred to here as carbohydrate depolymerization. The distribution of products depends on the biomass composition, particle size, and rate and duration of heating.

In the fast pyrolysis process, biomass is heated rapidly in a high temperature environment, yielding a mix of liquid fuel (bio-oil), combustible gases, and solid char. Pyrolysis is an independent conversion technology, as well as a part of the gasification process. Gasification can be separated into two main stages: 1) solid devolatilization (pyrolysis) and 2) char conversion (combustion and gasification). Fast pyrolysis converts biomass into liquid form, which has higher bulk density and heating value. Thus, it is easier and more economical to store and/or transport compared to the bulky biomass. The liquid product resulting from biomass pyrolysis is commonly referred to as "pyrolysis oil," "bio-fuel oil," or simply "bio-oil." Fast pyrolysis of biomass produces bio-oil, gas, and char. The gas stream containing $H_2$, CO, $CO_2$, and hydrocarbons can be used to provide the heat required for the pyrolysis. Char that is produced can be burned to provide heat for the pyrolysis, returned to the soil to enhance soil fertility, or recovered for sale (as activated carbon).

Pyrolysis can be carried out in batch, semi-batch and continuous modes. In batch processing, biochar is discharged after it has been cooled. Batch processing has several disadvantages. The energy cost is high, it is difficult to recover the volatiles formed during the process, pollution is a concern, and reaction sizes are limited. Semi-batch processing has the advantages that it is portable and allows recycling of heat containing vapors. The capacity is determined by the number of batch runs that can be carried out. Some semi-batch systems allow recovery of liquid products, but are typically limited to biochar recovery.

In one embodiment of the present invention, the pyrolysis mode is continuous mode pyrolysis.

Continuous mode pyrolysis is designed to run continuously, with occasional down time for maintenance. Continuous fast pyrolysis is suitable for high volume processing, and allows for the separation and collection of liquid bio-oil, combustible gases, and solid char. Any suitable reactor capable of carrying out continuous mode pyrolysis may be utilized.

Pyrolysis reactors may be characterized by the movement of solids through the reactor during pyrolysis and by the method of heat supplied. In batch reactors, solids typically do not move through the reactor during pyrolysis. In semi-batch and continuous reactors, movement may be facilitated by moving beds (i.e. shaft furnaces), mechanical forces (i.e. rotary kiln or rotating screws), or fluid flow (i.e. fluidized bed, spouted bed, entrained bed, etc). Heat may be supplied to biomass through burning material within the reactor, transfer from the combustion of fuel outside the reactor, transfer from inert hot material (i.e. hot gases or sand in the reactor), or transfer through the reactor walls from an external source.

Non-limiting examples of pyrolysis reactors include fluidized bed (e.g., re-circulating fluidized bed and bubbling fluidized bed), ablative reactors, rotating cone reactors, auger reactors, screw reactors, vacuum reactors, transported bed reactors, and entrained flow reactors.

Fluidized bed reactors may be used for continuous fast pyrolysis, and have a number of advantages, including easy loading and removing of catalyst, excellent heat transfer and mixing characteristics, temperature control, and uniform catalyst distribution. In fluidized bed reactors, biomass particles are mixed with moving sand particles of a high-temperature fluid bed. Heat may be generated by combustion of the pyrolysis gases, and/or char, and transferred to the fluid bed by heating coils. Fluidized bed reactors may be modified or improved to include twin fluid beds with solids exchange, modified combustion chambers and heat exchange, collection systems for pyrolysis liquids, hot gas filtration, handling and combustion of char, modification or replacement of cyclones, etc. Existing modifications of fluidized bed reactors include circulating fluidized bed reactors and bubbling fluidized bed reactors. The circulating fluidized bed utilized a char/sand loop in which the recirculated sand is reheated by the combustion of pyrolysis char. The main advantage of the circulating fluidized bed reactor is the direct heat supply to the biomass by recirculation of sand, reheated by combustion of pyrolysis char. The bubbling fluidized bed reactor uses large bubbles in the fluidized bed, which, as a result is very nonhomogeneous, and is characterized by oscillations in pressure drop across the bed over time.

The thermoplastic properties of lignin can lead to agglomeration during fast pyrolysis of lignin rich biomass. Agglomeration of lignin during fast pyrolysis may cause difficulty in product recovery or in reactor cleaning for batch, semi-batch, or continuous mode pyrolysis. Agglomeration may prohibit the use of continuous mode fast pyrolysis of lignocellulosic biomass, or necessitates frequent maintenance cycles, severely reducing its efficiency.

In fluidized-bed reactors, for example, feeding may be inhibited due to melting and agglomeration of lignin resulting in blockage of feeding tubes. Lignin agglomeration may also contribute to clogging due to collection of tar or char in the bed, cyclone, condenser, and electrostatic precipitator. Lignin may also create sticky residues within the machinery, causing resistance and hindering feeding.

The treated lignin rich biomass of the present invention has modified thermoplastic properties leading to the reduction of agglomeration during continuous mode pyrolysis, compared to when the lignin rich biomass is not subject to said treating. Thermoplastic properties may be altered through chemical processes. For example, the functional groups responsible for melting and subsequent agglomeration of lignin may be modified by chemical treatment. Non-limiting examples of functional groups that may influence thermoplastic properties include phenolic hydroxyls, aldehydes, and carboxylic acid groups. Hydroxyl groups may react with the alkali metal hydroxide or alkaline earth metal hydroxide to form hydroxyl phenoxides or phenate salt. Carboxyl groups may react with the alkali metal hydroxide or alkaline earth metal hydroxide to form phenolic alcohols. Aldehyde groups may react with the alkali metal hydroxide or alkaline earth metal hydroxide to form phenolic alcohols and phenolic calcium carboxylates.

In one embodiment of the present invention, the alkali metal hydroxide or the alkaline earth metal hydroxide is selected from the group consisting of $Ca(OH)_2$, NaOH, KOH, and $Mg(OH)_2$.

Alkali metal hydroxides and alkaline earth metal hydroxides are strong bases that may act as a base catalyst in organic chemical reactions, and are capable of modifying the chemical structure of lignins.

In one embodiment of the present invention, the treating comprises mixing the lignin rich biomass and the alkali metal hydroxide or alkaline earth metal hydroxide in water to form a mixture and reducing the moisture content of the mixture. In this embodiment, it is contemplated that the alkali metal hydroxide or the alkaline earth metal hydroxide is present in the mixture in an amount of 1% to 10% (w/w) prior to reducing the moisture content of the mixture. It is also contemplated that the alkali metal hydroxide or the alkaline earth metal hydroxide is present in the mixture in an amount of 4% to 6% (w/w) prior to reducing the moisture content of the mixture. In other embodiments, the alkali metal hydroxide or the alkaline earth metal hydroxide may be present in the mixture in an amount of 0.1% to 20% (w/w) prior to reducing the moisture content of the mixture.

The mixing of the lignin rich biomass and the alkali metal hydroxide or alkaline earth metal hydroxide to form a mixture may be achieved by any manual or automated means sufficient for the treatment to be effective. Drying can be carried out under any atmospheric conditions sufficient for drying, including but not limited to air drying and heat drying, and for any period of time, including but not limited to several hours to overnight.

In one embodiment of the present invention, the treated lignin rich biomass has decreased levels of phenolic hydroxyls, aldehydes, and carboxylic acid groups relative to when the lignin rich biomass is not subjected to treating.

In another embodiment of the present invention, the treated lignin extract has increased levels of calcium hydroxyl phenoxides, phenolic calcium carboxylates, and phenolic alcohols relative to when the lignin rich biomass is not subjected to treating.

The levels of phenolic hydroxyls, aldehydes, carboxylic acid groups, calcium hydroxyl phenoxides, phenolic calcium carboxylates, and phenolic alcohols may be measured by any means known in the art, including but not limited to fourier transformation infrared spectroscopy (FTIR) and gas chromatography (GC).

In one embodiment of the present invention, the treated lignin rich biomass is recovered.

Another aspect of the present invention relates to a method of fast pyrolysis. The method comprises providing a lignin rich biomass, treating the lignin rich biomass with an alkali metal hydroxide or an alkaline earth metal hydroxide under conditions effective to reduce agglomeration, during pyrolysis, compared to when the lignin rich biomass is not subjected to said treating, and pyrolyzing the treated lignin rich biomass to produce pyrolysis products.

In this aspect of the present invention, processing prior to pyrolysis is carried out using the materials, methods, and equipment substantially as described above.

Continuous mode pyrolysis may be carried out using any reactor capable of continuous mode pyrolysis.

In one embodiment of the present invention, pyrolyzing is carried out in continuous mode.

In another embodiment of the present invention, pyrolyzing is carried out in a fluidized bed reactor.

Pyrolysis may be carried out for any length of time and any temperature appropriate for the conversion of lignin rich biomass to bio-oil, light gases, and solid char. Temperature may be consistent throughout the pyrolysis process, or may vary during the pyrolysis process.

In one embodiment of the present invention, pryolyzing is carried out for 1 to 3 hours.

In another embodiment of the present invention, pyrolyzing is carried out at temperatures of 450° C. to 600° C.

Pyrolysis products may find use directly, or it may be desirable to further upgrade or process the pyrolysis products. Bio-oil may find use directly for heat or power generation, and further processing may produce liquid transportation fuels or chemicals such as resins, fertilizers, acetic acid, flavorings, adhesives or sugars. Biochar may find use as a soil amendment useful for carbon-sequestration, retention of water, nutrients and agricultural chemicals, and prevention of water contamination and soil erosion. Gases may be collected for use as fuel, and may also be used to drive the pyrolysis process.

Processing the pyrolysis product may include removing or separating components of the product (e.g. solid char, particulate matter, bio-oil, light gases), at any stage during or after pyrolysis. Vapor products may be condensed and fractionated, for example, by the method of U.S. Pat. No. 8,476,480 to Brown et al, which is hereby incorporated by reference in its entirety.

The pyrolysis product recovered from the pyrolysis of the treated lignin rich biomass, with or without further processing, may exhibit properties such as a high yield of phenolic monomers in bio-oils.

In one embodiment of the present invention, the method further comprises reducing or removing particulate matter in the pyrolysis product.

In another embodiment of the present invention, the method further comprises condensing vapor products from the pyrolysis product following said reducing or removing.

In another embodiment of the present invention, the method further comprises fractionating the pyrolysis product following said reducing or removing.

In another embodiment of the present invention, the fractionating further comprises separating the pyrolysis product into separate bio-oil, and light gas fractions.

In another embodiment of the present invention, the bio-oils are rich in phenolic monomers.

EXAMPLES

Example 1—Materials

Lignin from acetosolv processing of corn stover was provided by Archer Daniels Midland (ADM). Lignin from supercritical hydrolysis of pine wood was provided by Renmatix. Lignin derived from enzymatic hydrolysis of cornstover was provided by POET. Lignin resulting from alkaline extraction of softwood was purchased from Sigma Aldrich. All experiments were performed with acetosolv lignin from ADM unless otherwise specified. Phenol and vanillin, used as model compounds to represent lignin-derived pyrolysis products, and calcium hydroxide were purchased from Sigma-Aldrich. Solvents including methanol, acetone, tetrahydrofuran, and 1, 4-dioxane, were also purchased from Sigma-Aldrich.

Example 2—Characterization of Lignin

Ultimate analysis of lignin samples was determined with a Vario Micro Cube CHN elemental analyzer (Elementar, Germany). Proximate analysis was performed by a Mettler Toledo TGA/DSC system. The sample was first heated to 105° C. at 10° C./min to determine moisture content. The temperature was increased to 900° C. at 10° C./min to determine volatile content. Finally, air was introduced at 900° C. for another 30 min to determine fixed carbon and ash content. Inorganics in the lignin were analyzed by Inductively Coupled Plasma-Optical Emission Spectrometer (ICP-OES) (Optima 8000, PerkinElmer). Volatile organic compounds in untreated lignin were measured by dissolving 1 g of lignin in 9 ml of methanol and analyzing using GC/MS.

Example 3—Lignin Pretreatment Method

A 950 g of as-received lignin was mixed with 50 g of $Ca(OH)_2$ in water at room temperature (equivalent to 5% concentration). The mixture was dried in an oven at 50° C. to remove water until the moisture content of the mixture dropped to below 5%. The pinewood lignin was also prepared using the same concentration of $Ca(OH)_2$.

Example 4—Pyrolysis Experiments

Fast pyrolysis of untreated and pretreated lignin was conducted in a lab scale, fluidized bed reactor. Detailed information of the reactor system can be found elsewhere (Kim et al., "Partial Oxidative Pyrolysis of Acid Infused Red Oak Using a Fluidized Bed Reactor to Produce Sugar Rich Bio-Oil," *Fuel* 130:135-141 (2014), which is hereby incorporated by reference in its entirety). Briefly, the reactor system consists of a biomass feeder, an injection auger, a stainless steel reactor, and a bio-oil recovery system. The pyrolytic vapors exiting the reactor passed through two stages of gas cyclones to remove biochar. This was followed by an electrostatic precipitator (ESP) at 90° C. and a condenser cooled to −10° C. The bio-oil recovered by the ESP is referred to as heavy oil, while the bio-oil collected in the condenser is referred to as light oil. Nitrogen was used as sweep gas, 9 standard liters per minute (SLPM) was introduced into reactor and 1 SLPM was purged through the feeding system. The feeding rate was set up at 100 g/h. Pyrolysis temperatures were 450, 500, 550, and 600° C., respectively. The tests were run in triplicate at each temperature and average mass yields were reported.

Pretreated lignin was also pyrolyzed in a Frontier micropyrolyzer (Frontier laboratory, Japan) coupled to an Agilent GC-MS/FID/TCD (7890B GC, 5977A MSD). Detailed description of the system can be found elsewhere (Bai et al., "Formation of Phenolic Oligomers During Fast Pyrolysis of Lignin," *Fuel* 128:170-179 (2014), which is hereby incorporated by reference in its entirety). In brief, 500 μg of sample was placed in a deactivated stainless cup and pyrolyzed in a micro furnace preheated to 500° C. Helium gas was used as the carrier gas to sweep pyrolytic vapor into online GC columns with split ratio of 50:1. The GC oven was set at 40° C., then ramped up to 280° C. at 6° C./min. The volatiles were identified by MS and quantified by FID. The standard compounds were purchased from Sigma-Aldrich.

Pyrolysis tests of untreated and pretreated enzymatic hydrolysis lignin and alkali lignin were performed by a Mettler Toledo TGA/DSC system. Approximately 10 mg of sample was placed in a 900 μL crucible. The sample was heated from 25 to 500° C. at 50° C./min. The char residue remained in crucible was collected to observe its agglomeration problem.

Example 5—Characterization of Pyrolysis Products

The amount of bio-oil was calculated by weighing the reactor parts and condenser bottles before and after runs. Total char amount includes the char recovered in the two cyclones and the char remaining in the bed. Non-condensable gases (NCG) were analyzed with a micro-GC (Varian CP-4900) and gas yields calculated using the ideal gas law based on the measurement from a drum-type gas meter (Ritter, Germany). Standard gas mixtures of CO, $CO_2$, $H_2$, $CH_4$, $C_2H_4$, $C_2H_6$, $C_3H_6$ and $C_3H_8$ were purchased from Praxair and calibrated for quantification of the gas yield.

The composition of bio-oil was analyzed using the Agilent GC-MS by replacing the micropyrolyzer with a liquid auto sampler. Water content of bio-oil was determined by Karl-Fisher titration (KEM, MKS-500). The acidity of bio-oil was measured by modified acid number (MAN) with titrator (Metrohm, 789 MPT Titrino). The acidity is measured as mg KOH/g bio-oil.

The molecular weight distribution of bio-oils was measured with a gel permeation chromatograph (GPC) (Ultimate 3000, DIONEX) equipped with a Shodex Refractive Index (RI) detector and a UV detector. Tetrahydrofuran was used as eluent at flow rate of 1 ml/min. The signal at 254 nm was used to calculate molecular weight distribution. Elemental composition of bio-oil and char was analyzed using the CHN analysis method described above.

FTIR (SMART iTR NICOLET iS10, Thermo Scientific) was used to analyze char. Each sample was scanned 32 times from 4000 cm-1 to 650 cm-1 with resolution of 4 cm-1. Inorganics in the bio-oil and char were analyzed using the ICR method described above. Brunauer-Emmet-Teller (BET) surface area of char was measured by nitrogen gas sorption analysis at 77 K using a physisorption analyzer (Micrometitics ASAP 2020). Approximately 0.2-0.3 g char was loaded into the sample tube. The sample was first degassed at 300° C. for 4 hours prior to analysis.

Scanning electron microscope (SEM) of char produced from untreated or pretreated lignin was conducted using a FEI Quanta-250 FE-SEM. For pH test, 1 g of char was added to 20 ml of deionized water and equilibrated for 1.5 hours on the shaker at room temperature and its pH value was determined using pH test strip.

Example 6—Comparison of Untreated and Pretreated Lignin Prior to Pyrolysis

Untreated or pretreated lignin was dissolved in acetone, methanol, tetrahydrofuran, and 1,4-dioxane. The solvent soluble fractions were filtered and the solvent was evaporated at 40° C. in a rotary evaporator. The insoluble fractions were dried at 50° C. in a vacuum oven. Both solvent soluble lignin fraction and insoluble fraction were weighed before heating to 450° C. for 1 min to test thermal agglomeration. Untreated and the solvent soluble fractions of untreated lignin were also analyzed in GPC for molecular weight distribution.

Untreated and pretreated lignins were also analyzed by FTIR. Prior to FTIR tests (FTIR method was described above), the lignin samples were placed in a vacuum oven at 50° C. for 72 hours to completely remove moisture and other volatiles.

Example 7—Model Compound Study

Phenol and vanillin were used as model compounds to better understand the mechanism by which pretreatment prevented lignin agglomeration. Phenol in the amount of 0.2 g was mixed with 0.16 g of $Ca(OH)_2$ in 5 ml of deionized water. The mixture was stirred for an hour and kept in a vacuum oven at 50° C. until water was removed. The same amount of vanillin was mixed with 0.04 g of $Ca(OH)_2$ in 1 ml of deionized water and otherwise prepared in the same manner as the phenol. Both untreated and $Ca(OH)_2$ treated phenol and vanillin samples were analyzed by FTIR.

Example 8—Performance of Untreated and Pretreated Lignin in Fluidized Bed Reactor The proximate and ultimate analysis results of lignin are given in Table 1. As-received lignin contained 6.1% of ash and also contained 2.25% of acetic acid as residue from the acetosolv process.

TABLE 1

Ultimate and proximate analysis of lignin.

| Ultimate analysis (wt %) | |
| --- | --- |
| Carbon | 61.34 |
| Hydrogen | 4.67 |
| Nitrogen | 2.00 |
| Sulfur | 0.20 |
| Oxygen* | 31.79 |
| Proximate analysis (wt %) | |
| Moisture content | 3.87 |
| Volatiles | 62.52 |
| Fixed carbon | 27.55 |
| Ash | 6.07 |

*Determined by difference

FIGS. 1A-D compare the visual appearance of untreated lignin and pretreated lignin prior to pyrolysis. Untreated lignin had a dark brown color (FIG. 1A) and the pretreated lignin showed a lighter color (FIG. 1B), both were fine powders.

To confirm that the untreated lignin used in this study melted and agglomerated upon heating, it it was pyrolyzed in the fluidized bed reactor at 500° C. as a control case. As expected, the pressure at the inlet of the biomass feeder started increasing immediately after the lignin was fed into the reactor. The operation was terminated after 40 min due to defluidization of the sand in the reactor. Upon disassembly of the reactor, large, smooth chunks of carbonaceous material were found in both the feeder tube and the reactor bed with sand-char agglomerates stuck to the bottom of the reactor (FIG. 1C). No char was recovered in the gas cyclones, suggesting that little char left the reactor. Agglomeration of char and absence of fine char in the cyclones were similarly observed in previous studies of (untreated) lignin pyrolysis (Nowakowski et al., "Lignin Fast Pyrolysis: Results From an International Collaboration," *J. Anal., Appl. Pyrol.* 88:53-72 (2010), which is hereby incorporated by reference in its entirety).

In comparison, pretreated lignins were successfully pyrolyzed at all temperatures attempted. Pressure did not increase at any point in the system and char agglomerates were absent from the reactor upon completion of the tests. Char was collected as fine particulate matter in the gas cyclones (FIG. 1D), as occurs for pyrolysis of whole biomass (Kim et al., "The Effect of Low-Concentration Oxygen in Sweep gas During Pyrolysis of Red Oak Using a Fluidized Bed Reactor," *Fuel* 124:49-56 (2014), which is hereby incorporated by reference in its entirety). Pretreated lignin was continuously pyrolyzed for three hours under very stable operation with no indication that experiments could not have been continued longer.

The technical lignins from organsolv processing of cornstover, supercritical hydrolysis of mixed hardwoods, enzymatic hydrolysis of cornstover, and alkali extraction of unknown plant material were pretreated with $Ca(OH)_2$ and pyrolyzed to determine whether the present method for overcoming lignin agglomeration was generalizable to other kinds of lignin. The appearance of the resulting pyrolysis chars with these other lignins are shown in FIGS. 2A-F. The untreated lignins all formed char agglomerates whereas the pretreated lignins produced fine char powders, similar to the behavior observed for organsolv lignin. Furthermore pretreated supercritical hydrolysis lignin was successfully pyrolyzed in the continuous fluidized reactor, producing fine char similar to that observed from organsolv lignin. Thus, the pretreatment can prevent char agglomeration during pyrolysis of a wide range of technical lignins. The technical lignins from organsolv processing of cornstover, supercritical hydrolysis of mixed hardwoods, enzymatic hydrolysis of cornstover, and alkali extraction of unknown plant material were pretreated with $Ca(OH)_2$ and pyrolyzed to determine whether the present method for overcoming lignin agglomeration was generalizable to other kinds of lignin. The appearance of the resulting slow pyrolysis chars produced from these other lignins is shown in FIGS. 2A-F. The untreated lignins all formed char agglomerates whereas the pretreated lignins produced fine char powders, similar to the behavior observed for organsolv lignin. Furthermore, pretreated supercritical hydrolysis lignin was successfully pyrolyzed in the continuous fluidized reactor, producing fine char similar to that observed from organsolv lignin. Thus, the pretreatment can prevent char agglomeration during pyrolysis of a wide range of technical lignins.

Example 9—Pyrolysis Product Distribution

Figure 3:
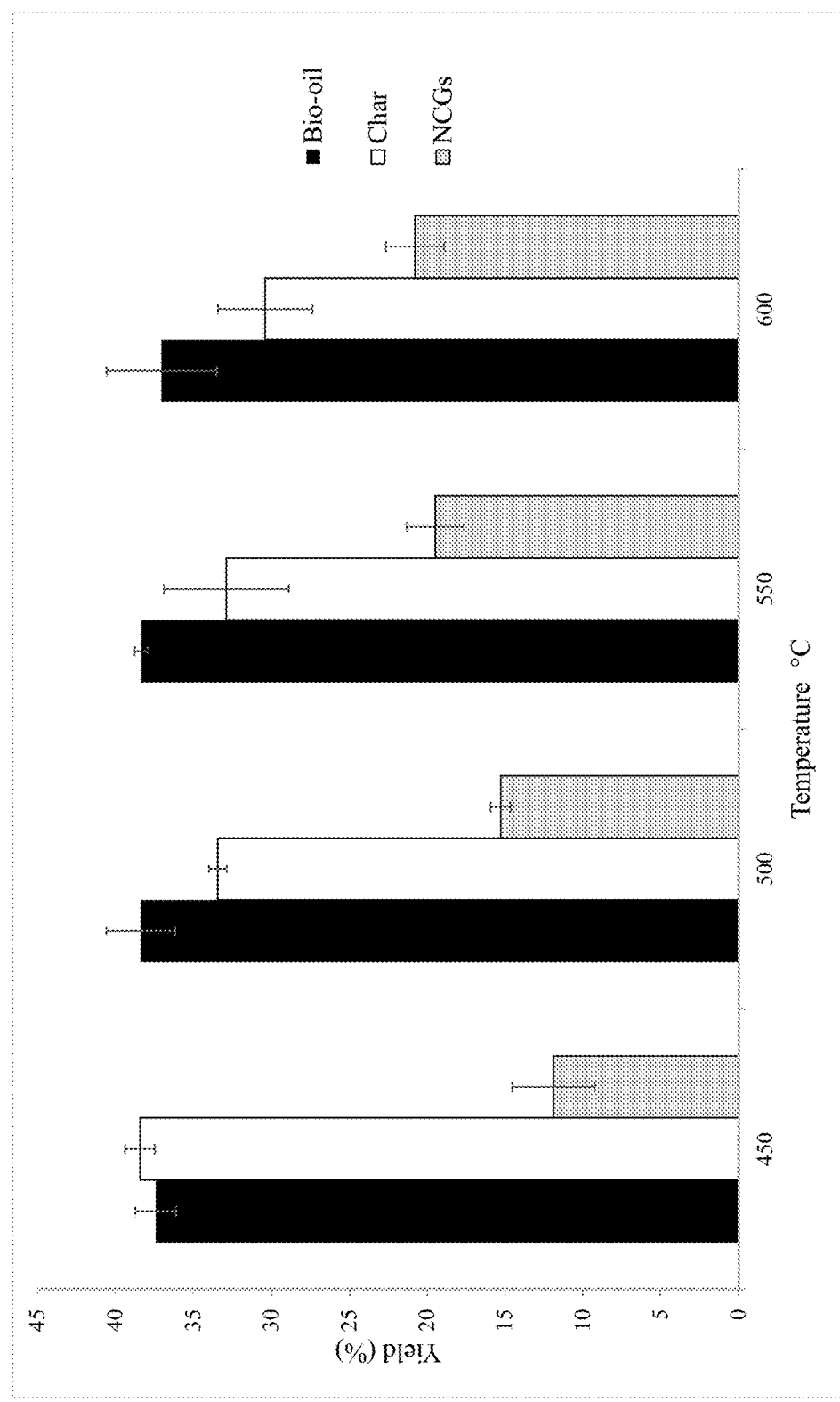
FIG. 3 shows the distribution of bio-oil, char, and non-condensable gases (NCG) from the pyrolysis of pretreated lignin at different pyrolysis temperatures, calculated on an ash-free and $Ca(OH)_2$-free basis for the feedstock lignin.

The distribution of pyrolysis products from pretreated acetosolv lignin is given in FIG. 3. The yields of bio-oil (the sum of heavy oil and light oil), char, and NCGs are reported on an ash- and $Ca(OH)_2$-free basis for the lignin feedstock. Mass closure was in the range of 87 to 90%. Bio-oil yield was not significantly influenced by temperature. The highest bio-oil yield was 38.4% at 500° C. with only slightly lower yields at other temperatures. Char yield decreased from 38.4 to 30.4% and NCG yield increased from 11.9 to 20.8% as temperature increased from 450 to 600° C. Previous researchers reported similar results for pyrolysis of lignin pretreated with clay or formate salt, with bio-oil yields of 23-44%, char yields of 35-41% and NCG yields of 15-39% even though the kinds of lignin were distinct from that of the present study (De Wild et al., "Lignin Pyrolysis for Profitable Lignocellulosic Biorefineries," *Biofuel Bioprod. Bior.* 8:645-657 (2014) and Mukkamala et al., "Formate-assisted Fast Pyrolysis of Lignin," *Energ. Fuel* 26:1380-1384 (2012), which are hereby incorporated by reference in their entirety).

Pyrolysis of technical lignin produced both higher yield of NCG and char and lower yield of bio-oil compared to pyrolysis of whole lignocellulosic biomass (Mullen et al., "Bio-Oil and Bio-Char Production From Corn Cobs and Stover by Fast Pyrolysis," *Biomass Bioenerg.* 34:67-74 (2010), which is hereby incorporated by reference in its entirety). It is hypothesized that technical lignin produces more char than lignin still contained in plant cell walls, because it contains more thermally stable bonds between aromatic rings.

Example 10—Characterization of Bio-Oil

Figure 4:
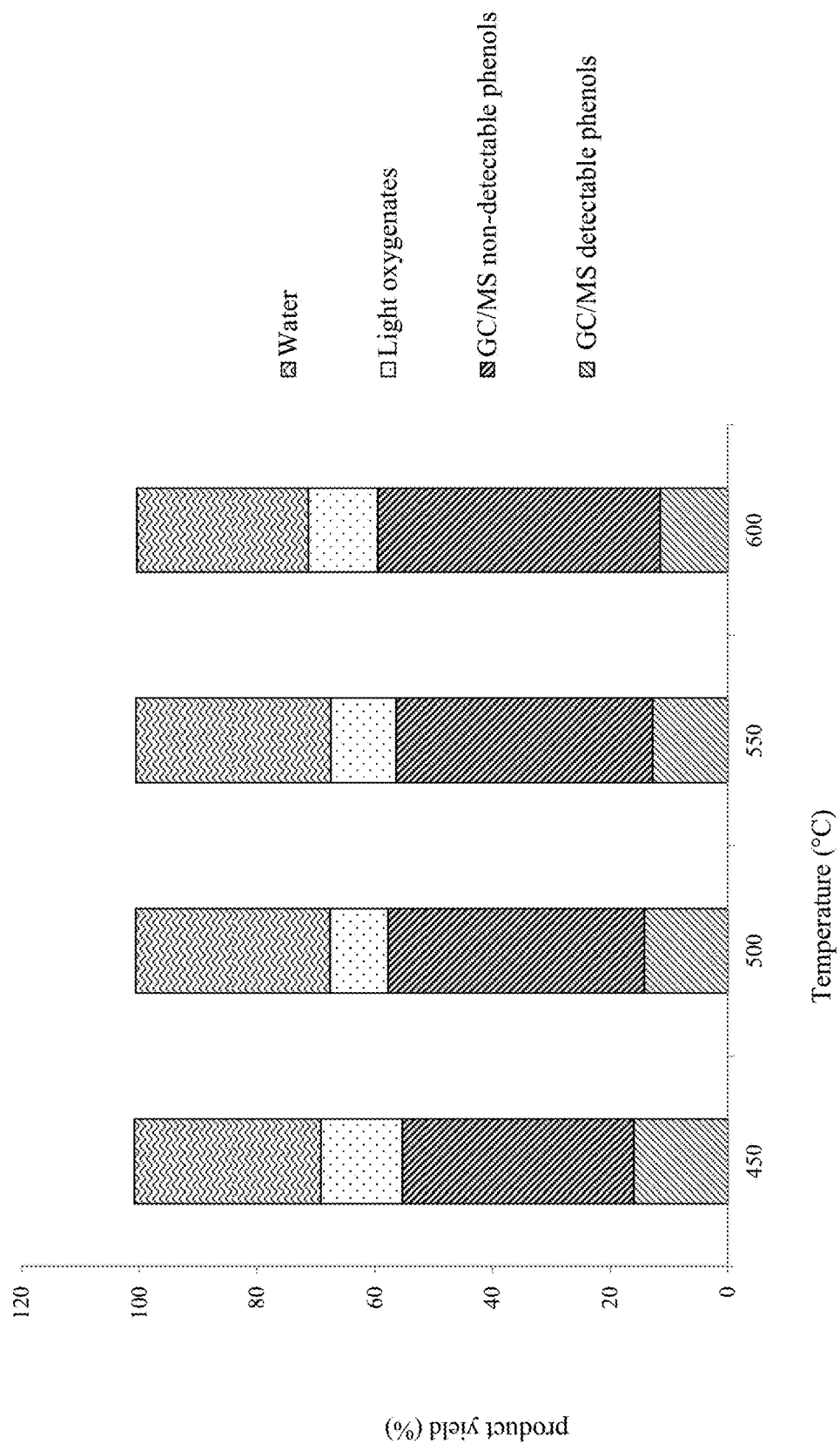
FIG. 4 shows the product distribution of bio-oil components as a function of pyrolysis temperature.
Figure 5A:
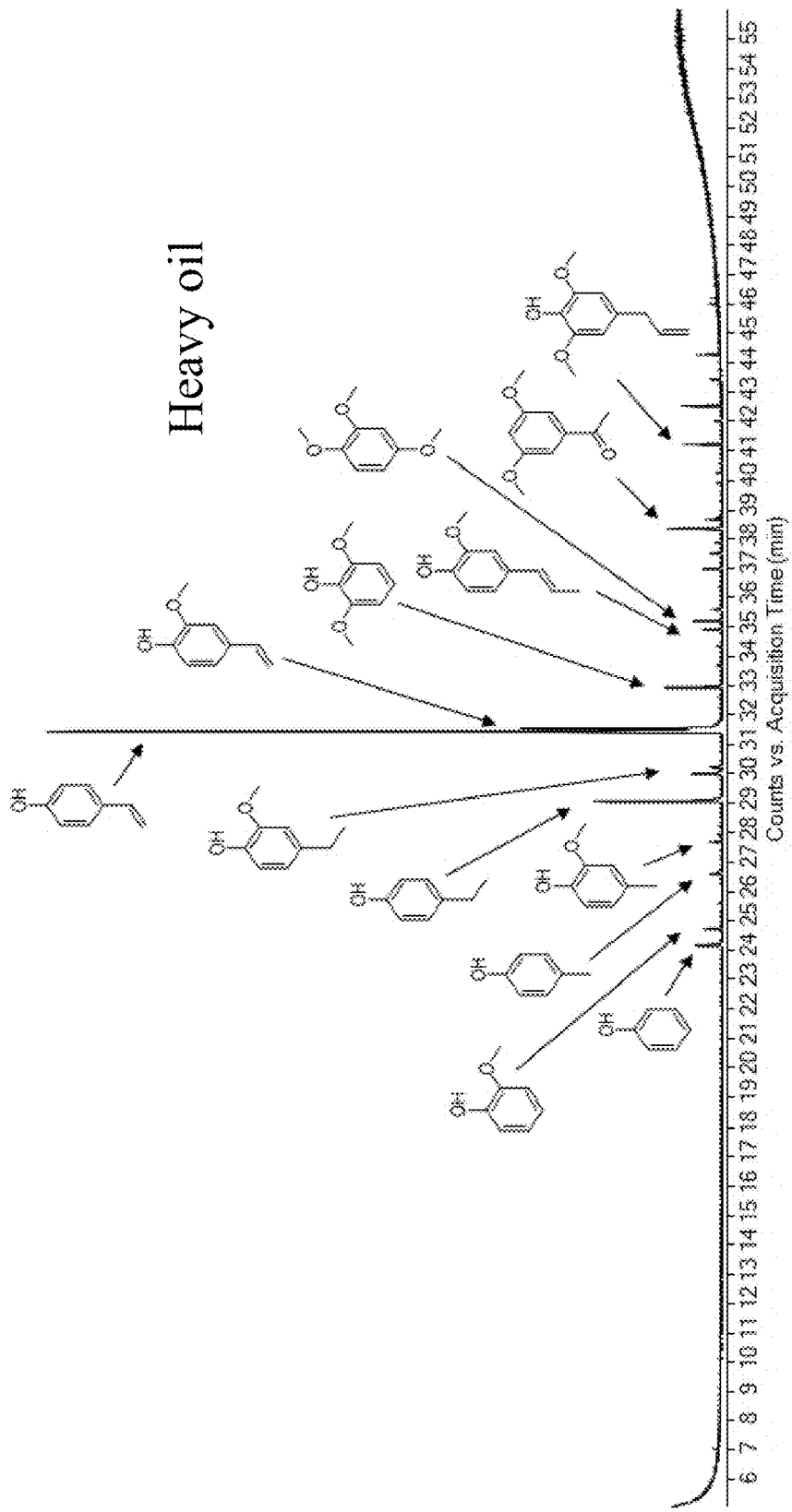
FIGS. 5A-B shows gas chromatography-mass spectrometery (GC/MS) chromatograms of oil produced from the pyrolysis of pretreated organosolv lignin at 500° C.
Figure 5B:
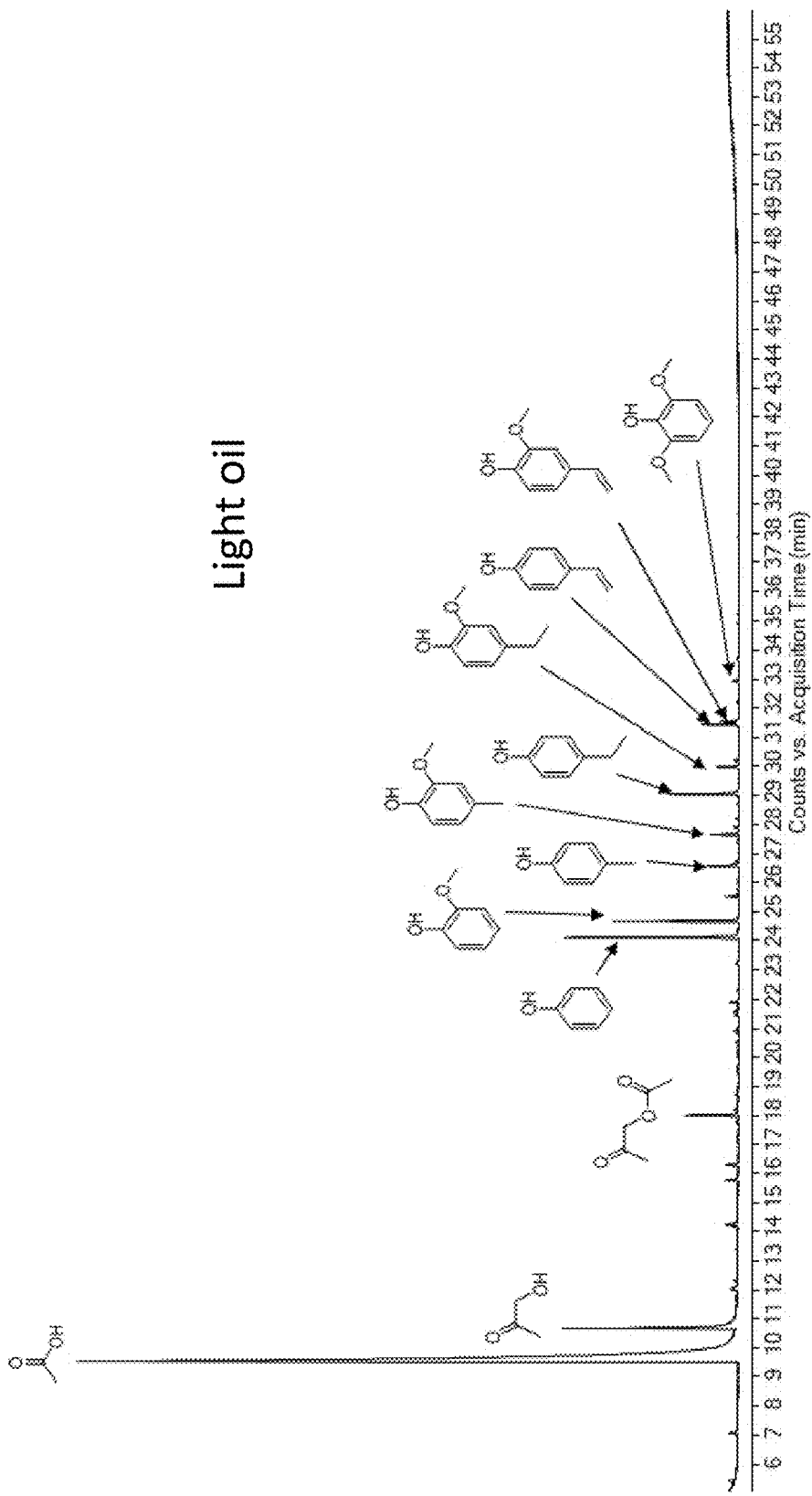

As shown in the properties of whole bio-oil listed in Table 2 (properties of the heavy and light oil fractions are provided in Table 3), up to 34.2% of the bio-oil was water. Up to 13.0% of bio-oil was light oxygenates (see Table 1 for detailed yields), mostly acetic acid derived from the solvent used in this acetosolv process. Acetol and acetol acetate were also found in bio-oil, derived from decomposition of carbohydrate residue in the lignin. However, the yields were low. The compositional distribution of the whole bio-oil is plotted in FIG. 4. This shows that 55-60% of the bio-oil was phenolic compounds. The GC/MS chromatograms in FIGS. 5A-B show that the bio-oil contains phenolic monomers from thermal depolymerization of lignin. Some examples include 4-vinylphenol, 2-methoxy-4-vinylphenol, guaiacol, syringol, phenol, trimethoxyl benzene, and ethyl, methylphenols. Vinylphenols were the major monomers derived from ether cleavage of lignin. The GC/MS-detected phenolic monomers accounted for up to 16% of whole bio-oil (equal to 6% per lignin weight). The yields of these phenolic monomers were lower than that were quantified by analyzing pyrolysis vapor before condensing determined by pyrolyzing the pretreated lignin in the micropyrolyzer (11.8% per lignin weight). The decrease in vinylphenols and other phenolic monomers in bio-oil due to polymerization catalyzed by acetic acid has been previously reported (Patwardhan et al., "Understanding the Fast Pyrolysis of Lignin," *ChemSusChem* 4:1629-1636 (2011) and Kim et al., "Quantitative Investigation of Free Radicals in Bio-Oil and Their Potential Role in Condensed-Phase Polymerization," *ChemSuSChem* 8:894-900 (2015), which are hereby incorporated by reference in their entirety).

TABLE 2

| Properties of Total Bio-Oil | | | | |
|---|---|---|---|---|
| Temperature (° C.) | 450 | 500 | 550 | 600 |
| Water (% in bio-oil) | 31.78 | 33.11 | 34.18 | 29.23 |
| Molecular weight distribution | | | | |
| Mw (Da) | 274 | 288 | 268 | 252 |
| Mn (Da) | 167 | 174 | 170 | 157 |
| PD | 1.66 | 1.66 | 1.56 | 1.58 |
| MAN (mg KOH/g) | 119.52 | 104.78 | 118.13 | 145.50 |
| Elemental composition (%) | | | | |
| C | 43.90 | 46.18 | 42.69 | 41.87 |
| H | 6.92 | 7.55 | 6.84 | 6.55 |
| O* | 47.66 | 44.51 | 48.57 | 49.54 |
| N | 1.50 | 1.73 | 1.86 | 2.02 |
| S | 0.03 | 0.03 | 0.02 | 0.02 |
| Heating value (MJ/kg)** | | | | |
| As-is bio-oil | 18.35 | 19.11 | 16.29 | 15.41 |
| Dry bio-oil | 23.92 | 27.52 | 23.64 | 20.91 |

*by difference
**calculated based on the formula provided in Demirbas "Calculation of Higher Heating Values of Biomass Fuels" *Fuel* 76: 431-4 (1997), which is hereby incorporated by reference in its entirety.

TABLE 3

Properties of Heavy Oil and Light Oil.

| Temperature (° C.) | | 450 | 500 | 550 | 600 |
|---|---|---|---|---|---|
| Bio-oil yield (%) | Heavy oil | 20.93 | 22.53 | 20.28 | 18.25 |
| | Light oil | 16.49 | 15.84 | 18.03 | 18.78 |
| Water (%) | In heavy oil | 5.48 | 3.24 | 2.44 | 3.67 |
| | In light oil | 65.17 | 75.59 | 69.89 | 54.06 |
| | Based lignin based | 11.89 | 12.70 | 12.71 | 10.83 |
| Molecular weight distribution | Heavy oil | | | | |
| | Mw (Da) | 288 | 297 | 290 | 300 |
| | Mn (Da) | 181 | 182 | 180 | 180 |
| | PD | 1.59 | 1.63 | 1.61 | 1.67 |
| | Light oil | | | | |
| | Mw (Da) | 224 | 239 | 187 | 153 |
| | Mn (Da) | 119 | 131 | 134 | 109 |
| | PD | 1.88 | 1.82 | 1.40 | 1.40 |
| MAN (mg KOH/g) | Heavy oil | 38.99 | 34.70 | 32.85 | 37.48 |
| | Light oil | 221.73 | 204.47 | 214.05 | 250.48 |
| Elemental composition (%) | Heavy oil | | | | |
| | C | 67.98 | 68.89 | 69.39 | 69.94 |
| | H | 6.99 | 6.97 | 6.87 | 6.06 |
| | O* | 23.05 | 21.85 | 21.31 | 21.47 |
| | N | 1.93 | 2.25 | 2.39 | 2.50 |
| | S | 0.05 | 0.04 | 0.04 | 0.03 |
| | Light oil | | | | |
| | C | 13.33 | 13.88 | 12.66 | 14.59 |
| | H | 6.82 | 8.38 | 6.81 | 7.02 |
| | O* | 78.89 | 76.75 | 79.24 | 76.82 |
| | N | 0.95 | 0.98 | 1.27 | 1.55 |
| | S | 0.01 | 0.01 | 0.02 | 0.02 |
| Heating value (MJ/kg)** | Heavy oil | 28.90 | 29.31 | 29.4 | 28.38 |
| | Light oil | 4.97 | 4.61 | 1.54 | 2.81 |

*by difference
**calculated based on the formula provided in Ogata et al., "Effects of Crosslinking on Physical Properties of Phenol-Formaldehyde Novolac Cured Epoxy Resins" *J. Appl. Polym. Sci.* 48: 583-601 (1997), which is hereby incorporated by reference in its entirety.

Figure 6:
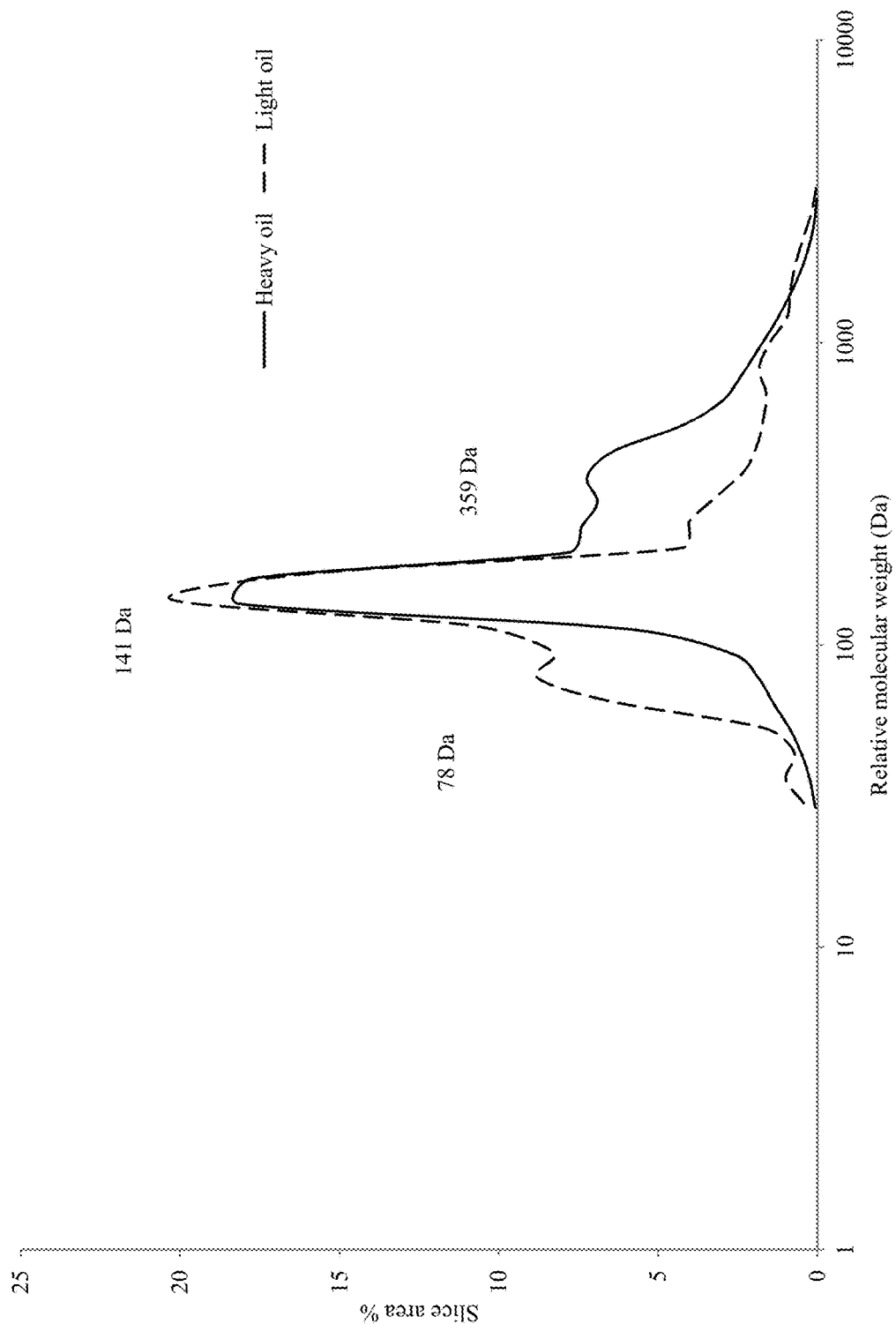
FIG. 6 shows the molecular weight distribution of heavy oil and light oil produced at 500° C., analyzed by gel permeation chromatography.

As shown in Table 2, the average molecular weight (MW) of whole bio-oil ranged from 252 to 288 Da with maximum molecular weight occurring for bio-oil produced at 500° C. Polydispersity (PD) was below 1.66 for bio-oil produced at various temperatures (Table 2). In the GPC chromatograms of bio-oils given in FIG. 6, the major peak appears at 141 Da, which corresponds to phenolic monomers. The smaller peaks at 359 Da and 78 Da represent phenolic dimers (Scholze et al., "Characterization of the Water-Insoluble Fraction from Fast Pyrolysis Liquids (Pyrolytic Lignin): Part II. GPC, Carbonyl Group, and $^{13}$C-NMR," *J. Anal., Appl. Pyrol.* 58-59:387-400 (2001), which is hereby incorporated by reference in its entirety) and light oxygenates, respectively. These results suggest that phenolic monomers represent the majority of UV detectable compounds in bio-oil (i.e., phenols and light oxygenates). Although GC/MS analysis indicated a lesser amount of phenolic monomers, this is probably because GC/MS is not able to detect many higher boiling point phenolic monomers (Bai et al., "Formation of Phenolic Oligomers During Fast Pyrolysis of Lignin," *Fuel* 128:170-179 (2014) and Smith et al., "Bio-Oil Analysis Using Negative Electrospray Ionization: Comparative Study of High-Resolution Mass Spectrometers and Phenolic Versus Sugaric Components," *Energ. Fuel* 26:3796-3802 (2012), which are hereby incorporated by reference in their entirety). Despite the condensation and repolymerization reactions possibly occurred during storage (Kim et al., "The Effect of Low-Concentration Oxygen in Sweep Gas During Pyrolysis of Red Oak Using a Fluidized Bed Reactor," *Fuel* 124:49-56 (2014), which is hereby incorporated by reference in its entirety), average MW of bio-oil was very low, suggesting the pretreated lignin was intensively depolymerized during fast pyrolysis.

As shown in Table 2 and Table 3, bio-oil acidity is mostly due to the presence of acetic acid. Higher pyrolysis temperatures increased acidity. The oxygen content of the bio-oil was similar to the carbon content, in the range of 40-50%, due to the high moisture content of the oil. Bio-oil produced at 500° C. had the highest carbon and hydrogen content and lowest oxygen content. Nitrogen was also present in lignin-derived bio-oil, similar to what is found in bio-oil derived from whole biomass (Elliot et al., "Catalytic Hydroprocessing of Biomass Fast Pyrolysis Bio-Oil to Produce Hydrocarbon Products," *Environ. Prog. Sust. Energ.* 28:441-449 (2009), which is hereby incorporated by reference in its entirety). Bio-oil produced at 500° C. had higher heating value (HHV) of 19.1 MJ/kg, which is similar to that of bio-oil produced from pyrolysis of whole biomass at comparable temperature (Mullen et al., "Bio-Oil and Bio-Char Production From Corn Cobs and Stover by Fast Pyrolysis," *Biomass Bioenerg.* 34:67-74 (2010), which is hereby incorporated by reference in its entirety).

As given in Table 4, lignin bio-oil contained only small amounts of Ca, Fe, S, and P despite the presence of a significant amount of these metals in the lignin and introduced during the pretreatment process. The inorganics mostly remain in the char, as further discussed in infra.

TABLE 4

ICP-OES Analysis of Untreated Lignin and Bio-Oil and Char from the Pyrolysis of Pretreated Lignin at 500° C.

| Inorganic (%) | Al | Ca | Cu | Fe | Mg | Mn | P | S | Zn | Na | K |
|---|---|---|---|---|---|---|---|---|---|---|---|
| Lignin* | 0.36 | 0.60 | — | 0.39 | 0.09 | 0.02 | 0.26 | 0.20 | — | 0.03 | 0.64 |
| Bio-oil | — | 0.04 | — | — | — | — | — | 0.03 | — | — | 0.01 |
| Char** | 0.74 | 7.59 | — | 0.81 | 0.21 | 0.03 | 0.55 | 0.20 | — | 0.07 | 1.36 |

— Non-detectable
*untreated
**pyrolysis char of pretreated lignin

Example 11—Gas Products

Detailed composition of gaseous products is given in Table 4. $CO_2$ was the major NCG followed by CO. Overall all NCGs increased with increasing pyrolysis temperature (Table 5). The yield of $CO_2$ was much higher than the yield of CO, similar to what was observed when the untreated lignin was pyrolyzed in a micropyrolyzer (Patwardhan et al., "Understanding the Fast Pyrolysis of Lignin," *ChemSusChem* 4:1629-1636 (2011), which is hereby incorporated by reference in its entirety).

TABLE 5

Yields of non-condensable gases

| Temp (° C.) | $H_2$ (%) | $CH_4$ (%) | $C_2H_4$ (%) | $C_2H_6$ (%) | CO (%) | $CO_2$ (%) |
|---|---|---|---|---|---|---|
| 450 | 0 | 0.64 | 0.19 | 0.2 | 1.88 | 10.12 |
| 500 | 0.1 | 1.41 | 0.19 | 0.29 | 2.53 | 10.76 |
| 550 | 0.23 | 1.89 | 0.37 | 0.25 | 3.85 | 12.88 |
| 600 | 0.24 | 1.88 | 0.44 | 0.3 | 4.46 | 12.1 |

Example 12—Characterization of Pyrolysis Char

Figure 7A:
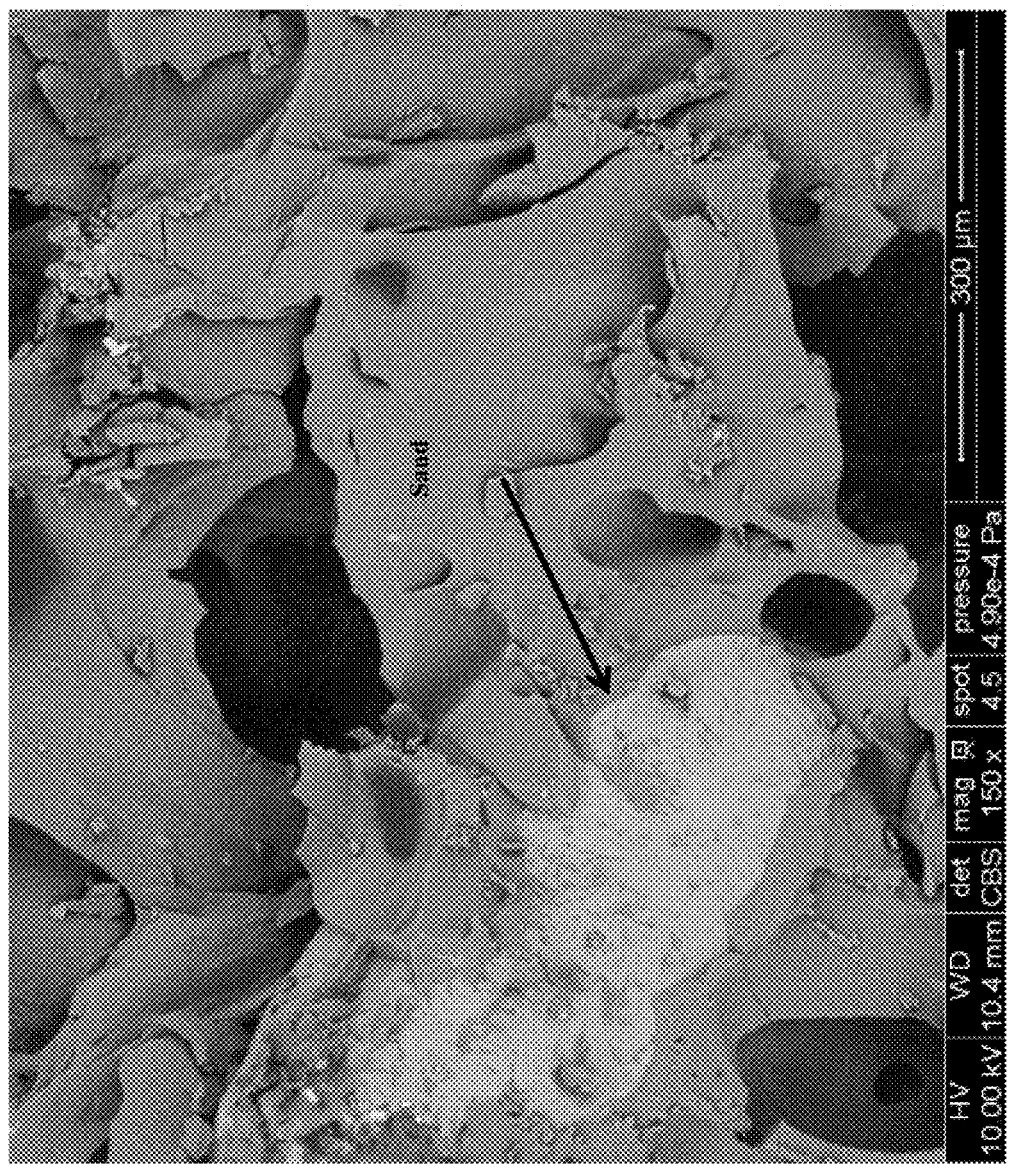
FIGS. 7A-B show scanning electron microscope (SEM) images of chars obtained from the pyrolysis lignin at 500° C.
Figure 7B:
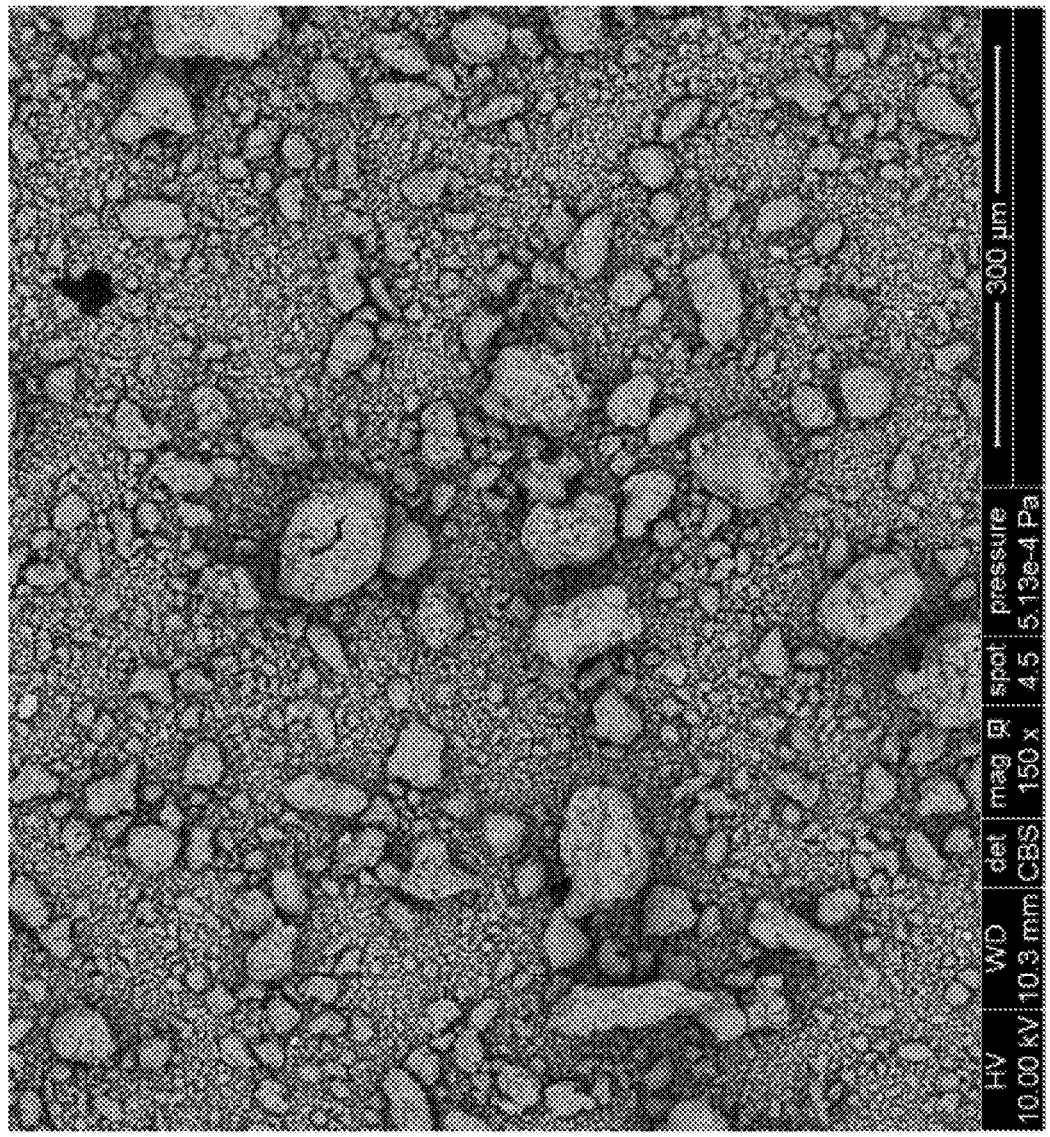

The SEM images of the char produced from untreated and pretreated lignin are compared in FIGS. 7A-B. The char from untreated lignin was smooth structured with imbedded sand particles, indicating that the lignin particles melted together, forming liquid that subsequently dehydrated to form agglomerated char (Sharma et al., "Characterization of Chars From Fast Pyrolysis of Lignin," Fuel 83:1469-1482 (2004), which is hereby incorporated by reference in its entirety). The microstructure of char from pyrolysis of pretreated lignin was quite different, with no evidence of melting and particle shapes similar to that of the lignin powders prior to pyrolysis.

Figure 8:
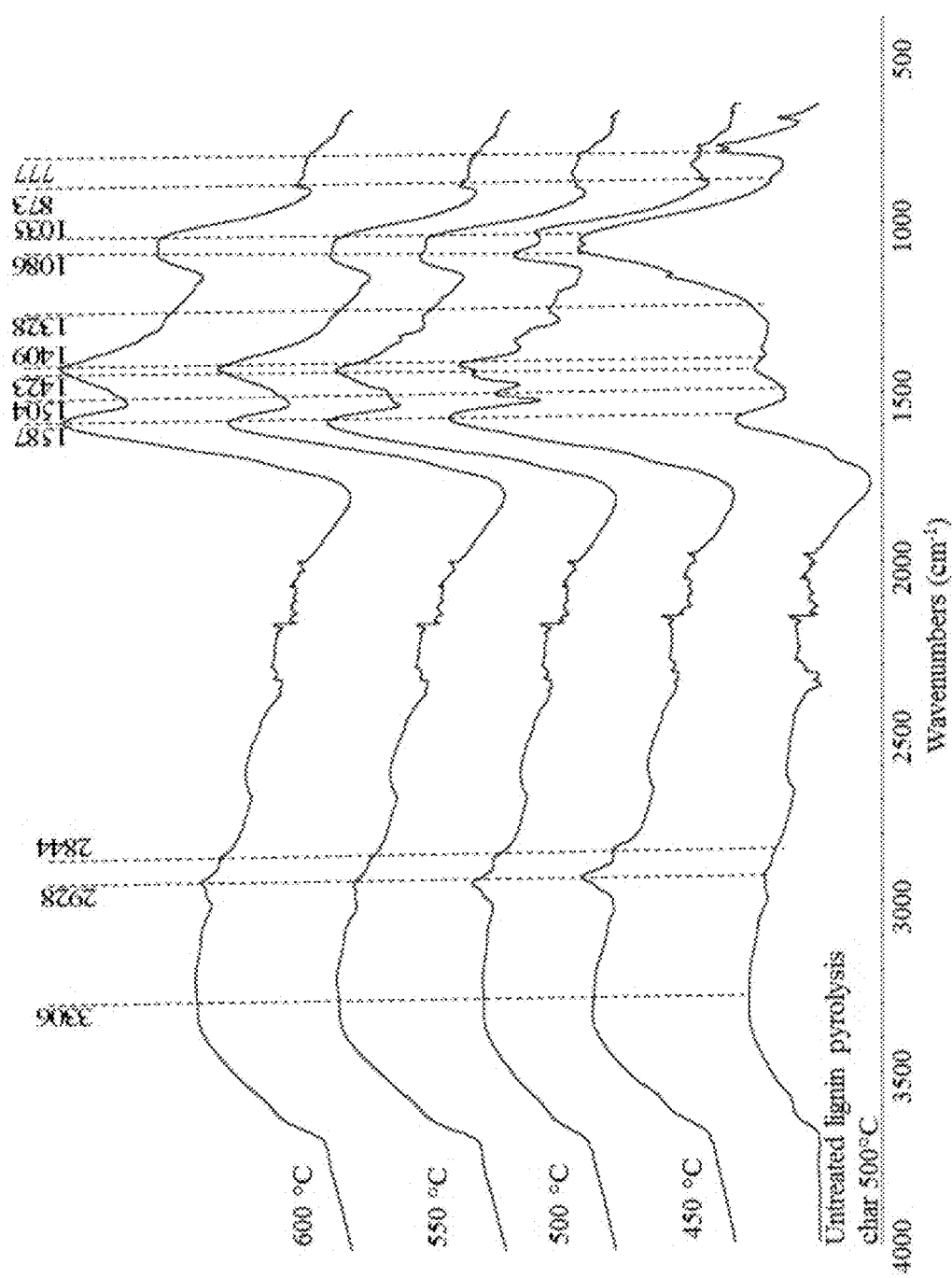
FIG. 8 shows fourier transform infrared spectroscopy (FTIR) spectra of char from the pyrolysis of untreated lignin at 500° C. and the pyrolysis of pretreated lignin at several temperatures.

FTIR spectra of chars are given in FIG. 8. Peaks correspond to OH (3306 cm-1), methyl (2928 cm-1) and methoxyl (2844 cm-1). Aromatic skeleton vibrations are represented by 1589, 1504, and 1423 cm-1. The peak at 1328 cm-1 is syringol plus guaiacol ring condensed. The shift in the band at 1423 to 1409 cm-1, along with a newly formed band centered at 873 cm-1 confirms the presence of CaO in the chars of pretreated lignin. The undulating peaks below 873 cm-1 are related to fused aromatic structures such as naphthalene, anthracene etc. Other bands at 1086 and 1035 cm-1 correspond to C—O deformation in alcohols and aliphatic ethers and also unconjugated C=O stretch. The bands between 1200-1300 cm-1 associated with C—C plus C—O plus C=O stretching. These bonds also continue to decrease at higher pyrolysis temperature due to decomposition of lignin structure at higher extent. Higher degree of demethoxylation and demethylation was also observed at higher pyrolysis temperature. Overall char of pretreated lignin had strong aromatic structure and it retained less C—O associated bonds.

Properties of char produced from fast pyrolysis of corn stover biomass (Brewer et al., "Extent of Pyrolysis Impacts on Fast Pyrolysis Biochar Properties," J. Environ. Qual., 41:1115-1122 (2012), which is hereby incorporated by reference in its entirety) and corn stover lignin are compared in Table 6. Ash content of char from corn stover biomass was significantly higher than char from corn stover lignin. Volatile matter and fixed carbon were higher in char obtained from pyrolysis of corn stover lignin than from cornstover biomass. Increasing pyrolysis temperature decreased the volatile content and increased the fixed carbon content of char from cornstover lignin. The BET surface area of char from corn stover lignin was in the range of 0.71 to 1 $m^2/g$, which is lower than for char from corn stover biomass. Previously, Sharma et al., "Characterization of Chars from Pyrolysis of Lignin," Fuel 83:1469-1482 (2004), which is hereby incorporated by reference in its entirety, also reported similarly low BET surface area for agglomerated char from lignin pyrolysis due to the melting of lignin particles. Pyrolysis of pretreated lignin did not produce micropores despite the absence of lignin melting. Carbon content of char from cornstover lignin was much higher than the char from corn stover biomass. Carbon content increased with increasing temperature accompanied by decreasing H and O. The char from corn stover lignin contained significantly higher amounts of nitrogen and sulfur than the char from corn stover biomass. At 500° C., N and S were 1.14 and 0.2% for char from corn stover lignin compared to 0.6 and 0.02% for char from corn stover biomass. HHV values of ash containing char from corn stover lignin were between 17.64 and 18.70 MJ/kg, much higher than for char from corn stover biomass (10.86 MJ/kg) probably due to its lower ash content. As shown in Table 4, the majority of inorganics in the original lignin and pretreated lignin were recovered in the char. Calcium accounted for 7.59% of lignin char obtained at 500° C. Potassium (K) was also the major inorganic in the char along with S, P and Fe. The pH of char from cornstover lignin slurried in water was between 8 and 9.

TABLE 6

Properties of Chars Produced from Pretreated Corn Stover Lignin and Corn Stover Biomass[a]

| | | | Char from corn Temperature (° C.) | | | | Char from corn stover stover biomass [a] |
|---|---|---|---|---|---|---|---|
| | | lignin | 450 | 500 | 550 | 600 | 500 [a] |
| Proximate analysis | Moisture | 2.85 | 3.08 | 3.42 | 3.46 | | 1.7 [a] |
| | Volatile | 39.27 | 33.82 | 30.16 | 29.25 | | 13.8 [a] |
| | Fixed C | 37.46 | 43.32 | 42.56 | 44.72 | | 25.2 [a] |
| | Fixed C/ volatiles | 0.95 | 1.28 | 1.41 | 1.53 | | 1.83 [a] |
| | Ash | 17.81 | 20.70 | 20.61 | 20.14 | | 59.3 [a] |
| BET surface ($m^2/g$) | | 1.00 | 0.78 | 0.71 | 0.89 | | 8.5 [a] |
| Elemental composition (%)[b] | C | 51.83 | 52.92 | 53.16 | 55.80 | | 29.5 [a] |
| | H | 3.26 | 2.68 | 2.43 | 2.32 | | 1.6 [a] |
| | N | 1.31 | 1.14 | 1.10 | 1.09 | | 0.6 [a] |
| | S | 0.20 | 0.20 | 0.20 | 0.25 | | 0.02 [a] |
| | O (by difference) | 25.60 | 22.36 | 22.5 | 20.40 | | 7.9 [a] |
| HHV(MJ/kg)[c] | | 17.86 | 17.94 | 17.64 | 18.70 | | 10.85 |

[a] Fast pyrolysis biochar of corn stover, data are from Brewer et al., "Extent of Pyrolysis Impacts on Fast Pyrolysis Biochar Properties," J. Environ. Qual., 41: 1115-1122 (2012), which is hereby incorporated by reference in its entirety;
[b] based on as-is pyrolysis char that containing ash and pretreatment agent;
[c] as-is char, calculated based on the formula provided in Demirbaş "Calculation of Higher Heating Values of Biomass Fuels," Fuel 76: 431-434 (1997), which is hereby incorporated by reference in its entirety.

Example 13—the Role of Ca(OH)$_2$ Pretreatment in Modifying Lignin Structure Continuous pyrolysis of the pretreated lignin can be carried out since it did not melt or agglomerate. After performing fractionation on the lignin using various solvents, it was found that the solvent-soluble fractions of lignin had a much stronger tendency to agglomerate during heat treatment than did the insoluble fractions. The average MWs of the solvent-soluble fractions were also lower compared to the solvent-insoluble fractions. It was also found that Ca(OH)$_2$ pretreatment of lignin reduced the solvent-soluble fractions of lignin. Mörck et al., "Fractionation of Kraft Lignin by Successive Extraction with Organic Solvents, I. 2240 Functional Groups, $^{13}$C NMR-spectra and Molecular Weight Distributions," Holzforschung 40:51-60 (1986), which is hereby incorporated by reference in its entirety, reported that lower MW fraction of lignin contains higher amount of phenolic OH and carboxylic acid groups than in the higher MW fraction of lignin. Sundin "Precipitation of Kraft Lignin Under Alkaline Conditions," *Institutionen för pappers—och massateknologi: KTH* (2000), which is hereby incorporated by reference in its entirety, on the other hand, reported that chemical binding of $Ca^{2+}$ with lignin increases its precipitation from solvent during kraft process. Thus, it is highly probable that the pretreatment process modified the functional groups that are responsible for melting and subsequence agglomeration of lignin.

Figure 9:
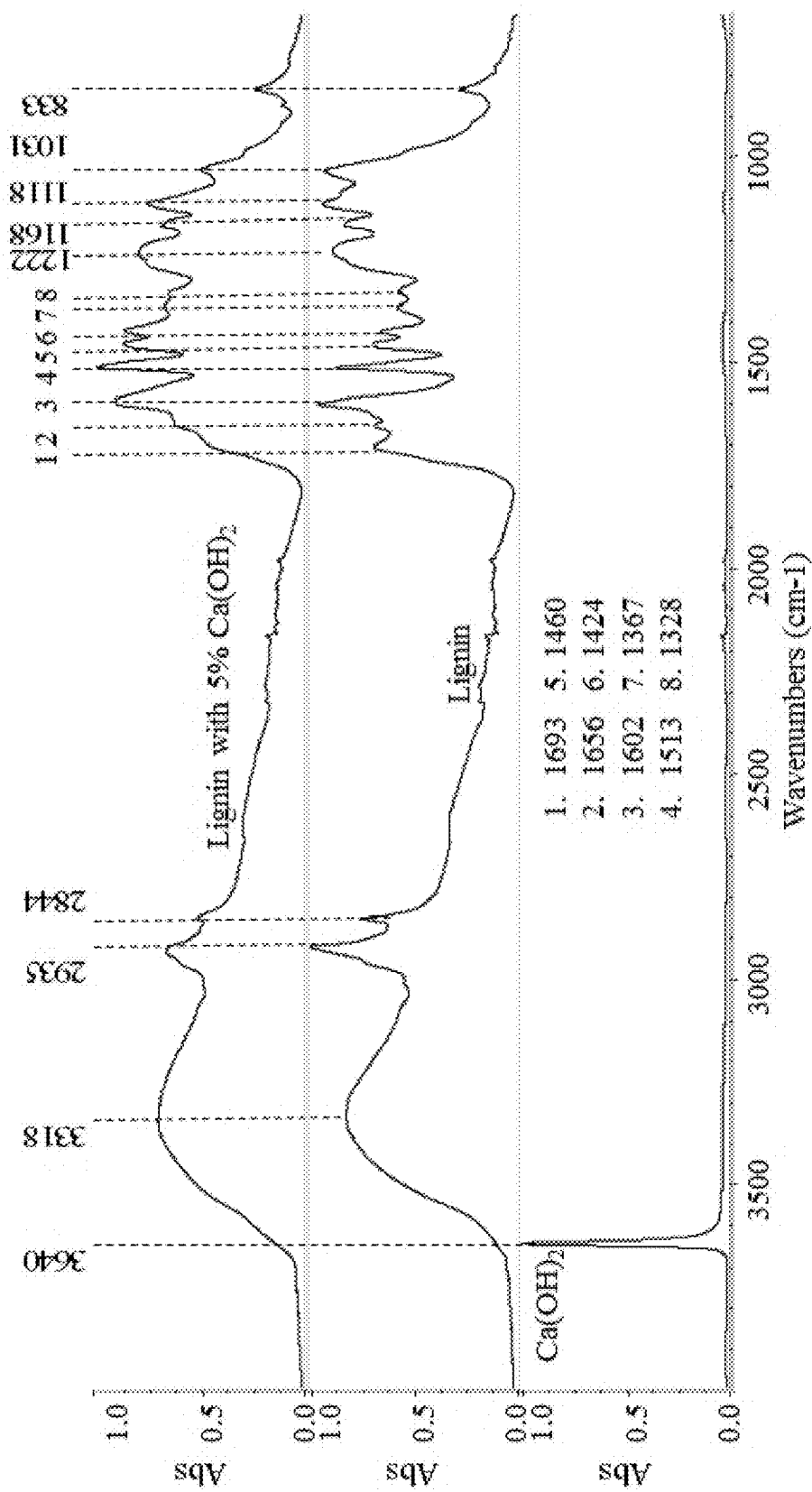
FIG. 9 shows FTIR spectra of untreated lignin, pretreated lignin and $Ca(OH)_2$.

FTIR spectra of the dried, pretreated lignin, moisture and acetic acid-free untreated lignin and calcium hydroxide are compared in FIG. 9. The spectrum of $Ca(OH)_2$ has a sharp peak at 3640 cm-1 for OH absorption whereas this peak was not apparent in the pretreated lignin samples, indicating $Ca(OH)_2$ reacted with lignin (Sundin "Precipitation of Kraft Lignin Under Alkaline Conditions," *Institutionen för pappers—och massateknologi: KTH* (2000), which is hereby incorporated by reference in its entirety) through chemical bonding. In lignin, the peak corresponding to OH (the broad peak centered at 3318 cm-1) also decreased upon pretreatment. While this peak could represent both phenolic OH and OH on side chain of benzene rings, it was also noted that the band with the peak at 1367 cm-1 which represents phenolic OH group also decreased. Thus, it is likely that phenolic OH decreased upon pretreatment.

Divalent cations like $Ca^{2+}$ could promote crosslinked structure of lignin by reacting phenolic OH group to form $Ca(aryl-O)_2$, promoting agglomeration and char formation. Since this did not occur in the experiments, more likely $Ca(OH)_2$ reacted with phenolic OH to form aryl-O—CaOH, which would discourage cross-linking. Evidence for this was reported by Schlosberg et al., "Organic Chemistry of Calcium. Formation and Pyrolysis of Hydroxycalcium Phenoxides,"*Energ. Fuel* 2:582-585 (1988), which is hereby incorporated by reference in its entirety, who observed that a slurry of phenol, with $Ca(OH)_2$, and water heated to 85-90° C. formed hydroxyl calcium phenoxide (PhO—Ca—OH). This was subsequently decomposed to phenol and CaO when pyrolyzed at 550-650° C. Phenol was recovered at near theoretical yield, which confirms that it did not cross-link via $Ca^{2+}$ as calcium diphenoxide would have formed irreversibly.

Figure 10:
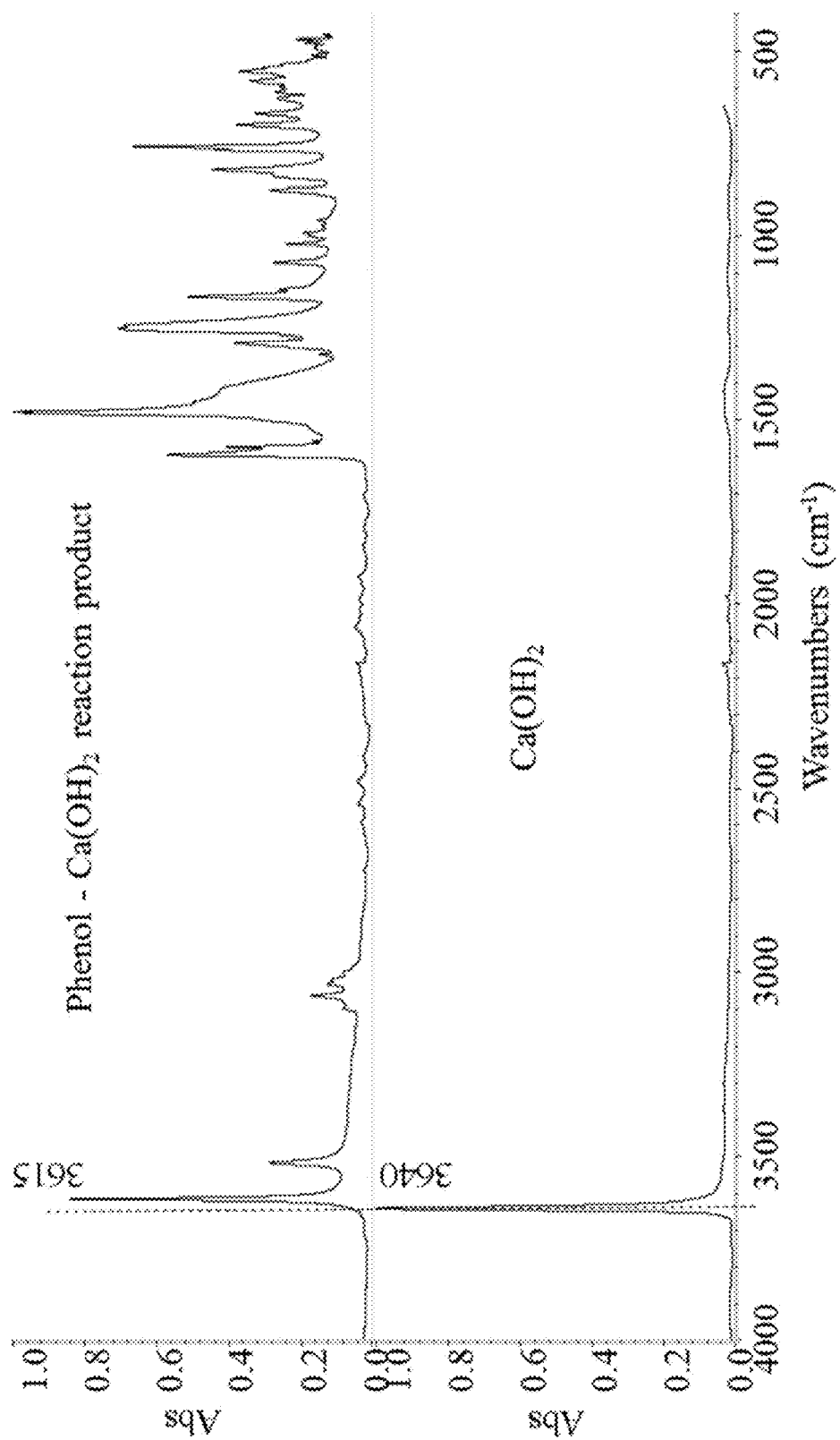
FIG. 10 shows an FTIR spectrum of the Ca(OH)$_2$ treated phenol at 50° C. (top) compared to an FTIR spectrum of Ca(OH)$_2$ (bottom).

Phenol was reacted with $Ca(OH)_2$ at 50° C., the same temperature at which pretreated lignin was dried, and the FTIR spectrum of the reaction product was compared with those of hydroxylcalcium phenoxide and calcium diphenoxide (Schlosberg et al., "Organic Chemistry of Calcium. Formation and Pyrolysis of Hydroxycalcium Phenoxides, "*Energ. Fuel* 2:582-585 (1988), which is hereby incorporated by reference in its entirety). This revealed the pretreated phenol to contain hydroxycalcium phenoxide rather than the crossed linked diphenoxide (FIG. 10). According to Schlosberg et al., "Organic Chemistry of Calcium. Formation and Pyrolysis of Hydroxycalcium Phenoxides,"*Energ. Fuel* 2:582-585 (1988), which is hereby incorporated by reference in its entirety, the peak at 3615 cm-1 and several smaller peaks with the wavenumbers below 700 cm-1 depicted in FIG. 10 do not appear at the spectrum of calcium diphenoxide but they appear for hydroxycalcium phenoxide.

Another significant change in the lignin IR spectrum after pretreatment was the complete elimination of the band centered on 1693 cm-1, which corresponds to conjugated aldehydes and carboxylic acids. Carboxylic functionality in lignin could react with $Ca(OH)_2$ to form either cross-linked $Ca(aryl-COO)_2$ or non-crosslinked aryl-COO—CaOH, although the inventors suspect it is more likely the latter based on the observations on reaction of phenol and $Ca(OH)_2$. Aldehydes could react with $Ca(OH)_2$ through the Cannizzaro reaction (Mizuno et al., "Synthesis and Utilization of Formose Sugars," *Advances in Carbohydrate Chemistry and Biochemistry, Acad. Press.* 173-227 (1974), which is hereby incorporated by reference in its entirety) to form phenolic alcohols and phenolic calcium carboxylates. After pretreatment, the band centered on 1656 cm-1, representing C=O stretch in conjugated p-substitute aryl ketones, combines with the peak for aromatic ring vibration (1602 cm-1) and becomes a broader peak shifted to the right due to C=O stretch (1592 cm-1) by calcium ion attachment. Hydroxylcalcium bonded phenolic structure would have lower solubility in organic solvents (Schlosberg et al., "Organic Chemistry of Calcium. Formation and Pyrolysis of Hydroxycalcium Phenoxides,"*Energ. Fuel* 2:582-585 (1988), which is hereby incorporated by reference in its entirety) and may explain the decreased solubility of pretreated lignin in solvents.

Figure 11A:
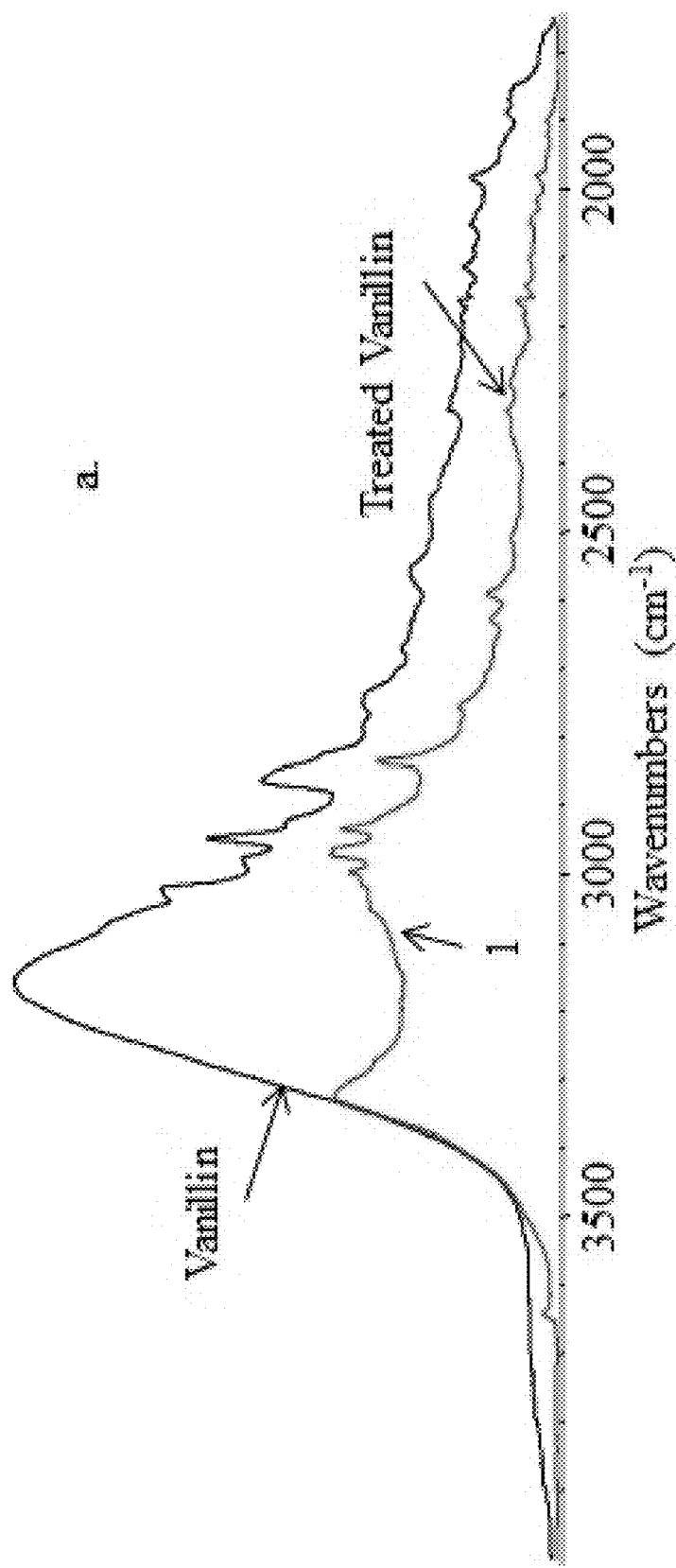
FIGS. 11A-B show an FTIR spectrum of vanillin and an FTIR spectrum of Ca(OH)$_2$ treated vanillin.
Figure 11B:
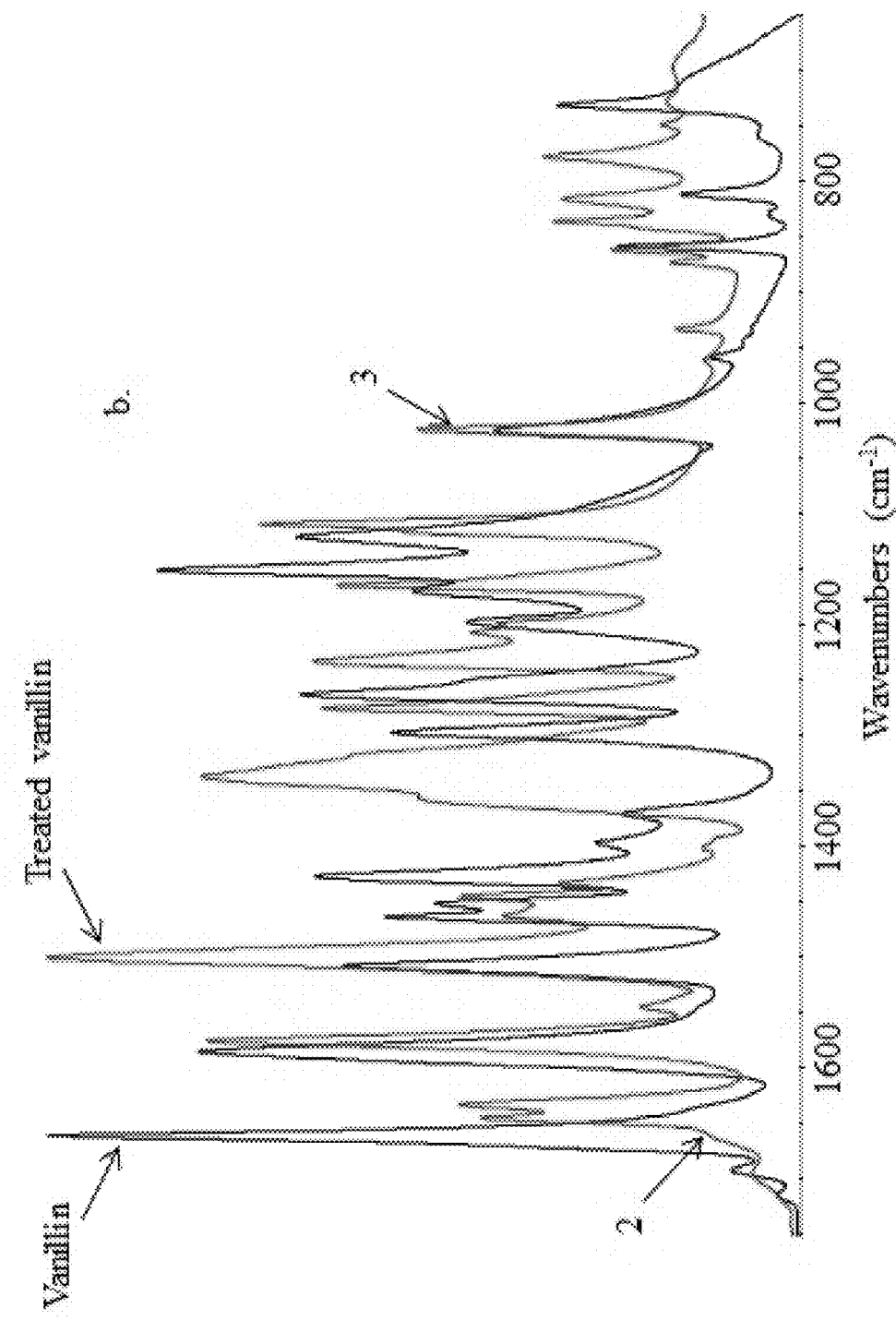

The proposed reaction mechanism was further explored by treating vanillin, a phenolic aldehyde that is also produced from lignin, with $Ca(OH)_2$ and analyzing with FTIR (FIGS. 11A-B). In the spectrum of $Ca(OH)_2$-treated vanillin, there was a dramatic decrease in phenolic OH, disappearance of aldehyde groups, and an increase in the alcohol group peak (1035 m-1) compared to untreated vanillin. A shift in the peak for C=O stretch due to Ca attachment was also found. The solubility of $Ca(OH)_2$-treated vanillin in solvent decreased and the color of treated vanillin also changed from white to yellow due to the loss of phenolic hydroxyl group.

The reactivity of phenolic hydroxyl or aldehyde groups for polymerization and crosslinking is well known (Ogata et al., "Effects of Crosslinking on Physical Properties of Phenol-Formaldehydr Novolac Cured Epoxy Resins," *J. Appl. Polym. Sci.* 48:583-601 (1993), which is hereby incorporated by reference in its entirety). Decreasing the content of these reactive functionalities in lignin by forming aryl-O—CaOH and aryl-COO—CaOH by $Ca(OH)_2$ pretreatment likely prevented polymerization of the phenols during pyrolysis to form resin-like polymers.

Figure 12:
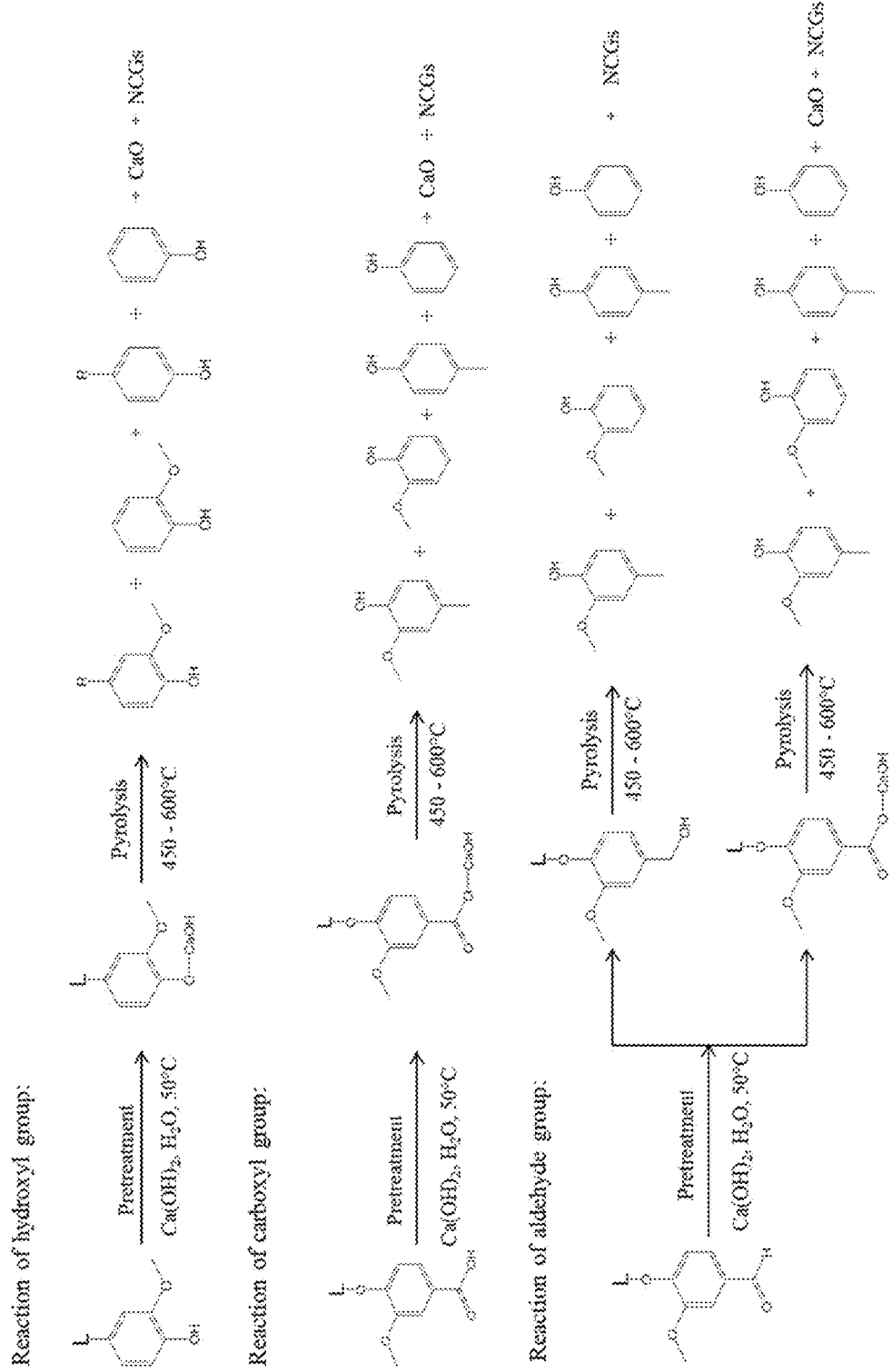
FIG. 12 shows the proposed reaction mechanism of lignin and calcium hydroxide during pretreatment and pyrolysis.

Pyrolysis of pretreated lignin is suspected of decomposing aryl-O—CaOH and aryl-COO—CaOH to phenolic compounds, CaO, $CO_2$, CO, and $H_2O$. The proposed reaction mechanism of $Ca(OH)_2$ and lignin during pretreatment and pyrolysis process are illustrated in FIG. 12.

The above findings suggest that phenolic hydroxyl, carboxylic acids, and aldehyde groups are likely responsible for agglomeration behavior of untreated lignin. Polymerization reactions among these functional groups are suspected of forming resin-like products at relatively low temperatures during pyrolysis. Dehydration of the liquid forms a large solid mass, thus impeding heat and mass transfer to and from the lignin particles. The fact that agglomerated char of untreated lignin still retains some of phenolic structure is evident in the FTIR spectrum of FIG. 6. The peaks at 777 cm-1 and 694 cm-1 (related to phenolic rings) only appeared in the agglomerated char of untreated lignin. Also, the bands associated with oxygen bonding and phenolic structure increased dramatically whereas the bands for aromatic ring vibration reduced significantly for (agglomerated) char from untreated lignin compared to (fine) char from pretreated lignin.

Technical lignin is successfully continuously pyrolyzed in a fluidized bed reactor without reactor modification. Pretreatment of the lignin by adding 5% $Ca(OH)_2$ prevented melting and agglomeration of lignin particles. Pyrolysis products included phenolic-rich bio-oil, light gases and fine char powder. Phenolic compounds in the bio-oil were mainly phenolic monomers and dimers with average MW less than 288 Da. Char from lignin was less porous compared to char from whole biomass and contained lower amounts of ash but significantly more N, S, K, and P. FTIR analysis of untreated and pretreated lignin suggests that phenolic hydroxyl, aldehydes and carboxylic acid groups are responsible for melting and agglomeration of lignin. $Ca(OH)_2$ pretreatment likely reduced or eliminated these functionalities by forming calcium hydroxyl phenoxides, phenolic calcium carboxylates and phenolic alcohols. Upon pyrolysis, Ca was converted to CaO and recovered in char.

Calcium hydroxide represents a low cost and low hazard pretreatment that is readily available. The amounts of $Ca(OH)_2$ required for pretreatment are very small, and easily recovered by burning the char and leaching the ash with water. The heat of combustion from this regeneration process can be used to heat the pyrolyzer. Alternatively, the char has potential as biobased fertilizer, and/or converted to activated carbon if the ash content of the lignin is relatively low.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of fast pyrolysis, said method comprising:
   (a) providing a technical lignin;
   (b) treating the technical lignin with an alkali metal hydroxide or an alkaline earth metal hydroxide in an amount of from over 4% (w/w) to 20% (w/w) under conditions effective to reduce agglomeration, during pyrolysis, compared to when the technical lignin is not subjected to said treating; and
   (c) pyrolyzing the treated technical lignin in continuous mode for 1 to 3 hours to produce pyrolysis products.

2. The method according to claim 1, wherein the technical lignin is produced by a process selected from the group consisting of organosolv process, supercritical hydrolysis, enzymatic hydrolysis, acid hydrolysis, alkaline extraction, solvent extraction, ionic-liquid extraction, and aprotic solvent extraction.

3. The method according to claim 1, wherein the alkali metal hydroxide or the alkaline earth metal hydroxide is selected from the group consisting of $Ca(OH)_2$, NaOH, KOH, and $Mg(OH)_2$.

4. The method according to claim 1, wherein said pyrolyzing is carried out in a fluidized bed reactor.

5. The method according to claim 1, wherein said treating comprises:
   mixing the technical lignin and the alkali metal hydroxide or the alkaline earth metal hydroxide to form an aqueous mixture having a moisture content and
   reducing the moisture content of the mixture.

6. The method according to claim 1, wherein said pyrolyzing is carried out at temperatures of 450° C. to 600° C.

7. The method according to claim 1 further comprising:
   reducing or removing particulate matter in the pyrolysis product.

8. The method according to claim 7 further comprising:
   condensing vapor products from the pyrolysis product following said reducing or removing.

9. The method according to claim 8 further comprising:
   fractionating the pyrolysis product following said reducing or removing.

10. The method according to claim 9, wherein said fractionating comprises:
    separating the pyrolysis product into separate bio-oil and light gas fractions.

11. The method according to claim 10, wherein said bio-oil is rich in phenolic monomers.

12. The method according to claim 1, wherein said treating is carried out without heating.

13. The method according to claim 1, wherein said treating is carried out at room temperature.

* * * * *